(12) United States Patent
Abe et al.

(10) Patent No.: US 8,700,373 B2
(45) Date of Patent: *Apr. 15, 2014

(54) METHOD FOR ESTIMATING SURVIVAL CELL COUNT, AND METHOD FOR SETTING GUARANTEED CELL COUNT

(75) Inventors: Fumiaki Abe, Yokohama (JP); Ayako Uchijima, Konan (JP); Ayako Horigome, Ebina (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 686 days.

This patent is subject to a terminal disclaimer.

(21) Appl. No.: 12/995,064

(22) PCT Filed: May 29, 2009

(86) PCT No.: PCT/JP2009/059881
§ 371 (c)(1),
(2), (4) Date: Nov. 29, 2010

(87) PCT Pub. No.: WO2009/145307
PCT Pub. Date: Dec. 3, 2009

(65) Prior Publication Data
US 2011/0112813 A1    May 12, 2011

(30) Foreign Application Priority Data
May 29, 2008 (JP) ................. 2008-140819

(51) Int. Cl.
*G06G 7/58* (2006.01)
*G06F 19/00* (2011.01)

(52) U.S. Cl.
CPC .................... *G06F 19/00* (2013.01)
USPC ........................................................ 703/11

(58) Field of Classification Search
USPC ........................................................ 703/11
See application file for complete search history.

(56) References Cited

PUBLICATIONS

Extended European Search Report issued in Patent Application No. 09754815.0, dated Aug. 23, 2011, 8 pages.
Cabaj, A. et al., Biodosimetry: Model Calculations for u.v. Water Disinfection Devices With Regard to Dose Distributions, Elsevier Science Ltd., 1996, pp. 1003-1009, vol. 30, No. 4.
Tatematsu et al.; "Effect of Water Activity on the Survival of Freeze-Dried Bifidobacteria and Lactic Acid Bacteria"; Dated 1982.
Damjanovic et al.; "Predicting the Stability of Freeze-Dried *Lactobacillus bifidus* by the Accelerated Storage Test"; Dated 1968.
Achour et al.; "Application of the Accelerated Shelf Life Testing Method (ASLT) to study the Survival Rates of Freeze-Dried *Lactococcus* starter cultures"; Dated 2001.
Ziadi et al.; "The Effect of Heat Stress on Freeze-Drying and Conservation of *Lactococcus*"; Dated 2001.
Portner et al.; "Optimising the Viability During Storage of Freeze-Dried Cell Preparations of *Campylobacter jejuni*"; Dated 2007.
Nagawa et al.; "Preparation of the Bifidus Milk Powder"; Dated 1987.
Takematsu et al.; "Effect of Water Activity on the Survival of Freeze-Dried Bifidobacteria and Lactic Acid Bacteria"; Dated 1982.
Simpson et al.; "Intrinsic Tolerance of *Bifidobacterium* Species to Heat and Oxygen and Survival Following Spray Drying and Storage"; Dated 2005.
Higl et al.; "Impact of Water Activity, Temperature, and Physical State on the Storage Stability of *Lactobacillus paracasei* ssp. *paracasei* Freeze-Dried in a Lactose Matrix"; Dated 2007.
Japanese Patent Office; Search Report in International Patent Application No. PCT/JP2009/059881; Dated Jun. 23, 2009.
Wijtzes et al.; "Development and Validation of a Combined Temperature, Water Activity, pH Model for bacterial Growth Rate of *Lactobacillus curvatus*"; Dated 2001.
Richard C. Whiting; "Microbial Database Building: What Have we Learned?"; Dated 1997.
European Patent Office, Search Report issued in Application No. 09754814.3, mailed Aug. 23, 2011, 9 pp.
Japanese Patent Office, International Search Report issued in Application No. PCT/JP2009/059880, mailed Jul. 21, 2009, 3 pp.
Abe et al., "Stability of bifidobacteria in powdered formula," International Journal of Food Science & Technology, 44:718-724, 2009.
Geeraerd et al., "Development of a novel approach for secondary modelling in predictive microbiology: incorporation of microbiological knowledge in black box polynomial modelling," Int. J. Food Microbiol., 91(3):229-244, 2004.
Kim et al., "Survival of Lactic acid Bacteria during Microwave Vacuum-drying of Plain Yoghurt," Lebensm-Wiss u-Technol., 30:573-577, 1997.
Lin et al., "Survival of *Enterobacter sakazakii* in infant cereal as affected by composition, water activity, and temperature," Food Microbiology, 24:767-777, 2007.

(Continued)

*Primary Examiner* — Jerry Lin
(74) *Attorney, Agent, or Firm* — Wood, Herron & Evans, LLP

(57) ABSTRACT

The present invention provides a method for estimating survival cell count, which is able to calculate an accurately estimated result of the survival cell count of a specific strain in a probiotic product with respect to its storage period, and to shorten the time for developing the product, and a method for setting a guaranteed cell count, which is able to readily calculate a guaranteed cell count of a specific strain in a probiotic product within its quality guarantee period. The method for estimating the survival cell count is characterized by estimating the survival cell count $n_t$ (CFU/g) of a specific strain contained in a composition after storage, in accordance with the following equation (I). (I) $\mathrm{Log}_{10}\ n_t = \mathrm{Log}_{10}\ n_0 - t \times \mathrm{EXP}\{(A_T \times T + B_T)w + (C_T \times T + D_T)\}$, provided that t stands for the storage period (days)$\times 1/30$, $n_t$ stands for the survival cell count (CFU/g) of the strain contained in the composition after the storage period t (days), $n_0$ stands for the viable cell count (CFU/g) of the strain contained in the composition at the initiation of storage, T stands for the storage temperature (° C.), w stands for the water activity value of the composition, $A_T$ and $C_T$ stand for experimentally determined coefficients specific to the strain, and $B_T$ and $D_T$ stand for experimentally determined constants specific to the strain.

11 Claims, 13 Drawing Sheets

(56) References Cited

PUBLICATIONS

Park et al., "Survival of *Escherichia coli* O157:H7 in potato starch as affected by water activity, pH and temperature," Letters in Applied Microbiology, 31:364-367, 2000.

Ziadi et al.; "The Effect of Heat Stress on Freeze-Drying and Conservation of *Lactococcus*"; Dated 2005.

Cabaj, A. et al., Biodosimetry: Model Calculations for u.v. Water Disinfection Devices With Regard to Dose Distributions, Water Research, 1996, pp. 1003-1009, vol. 30, No. 4.

METHOD FOR ESTIMATING SURVIVAL CELL COUNT, AND METHOD FOR SETTING GUARANTEED CELL COUNT

TECHNICAL FIELD

The present invention relates to a method for estimating survival cell count, and a method for setting a guaranteed cell count of a strain such as probiotics contained in a composition.

Priority is claimed on Japanese Patent Application No. 2008-140819, filed May 29, 2008, the content of which is incorporated herein by reference.

BACKGROUND ART

Bifidobacteria and lactic acid bacteria are used as probiotics for various kinds of foods. For example, bifidobacteria and lactic acid bacteria are prepared in forms of powders, capsules, tablets, and the like, for the application to a wide range of food products including health foods, confectioneries, and baby milk powder. Moreover, applications of bifidobacteria and lactic acid bacteria as probiotics to the fields of medical services and livestock foods have also started.

Probiotics confer a beneficial effect on the human and animal health by proliferating themselves inside the intestine when administered into the host human or animal. Therefore, it is important that probiotics are kept alive. Although it is very difficult to mix a *bifidobacterium* or a lactic acid bacterium in a product while maintaining its survival cell count within the guarantee period (best-before period), some techniques have been developed in the past, and now, many probiotic-containing foods, pharmaceuticals, and feeds (hereunder, referred to as probiotic products) are on the market.

For the development of probiotic products, a great number of items have to be examined, for example, it is necessary to predict the change in the survival cell count in the product, to set the best-before period of the product, and to check the efficacy of the product. In addition, it is also necessary to clarify the guaranteed cell count in the probiotic product within the guarantee period, in terms of the quality assurance of the product for the consumer.

For this reason, during the development of probiotic products, it is necessary to measure the survival cell count of a probiotic strain in the product within the storage period by performing an actual storage test so as to evaluate the probiotic survivability. However, as the guarantee period of probiotic products is often set as very long, as much as one to three years, it is necessary, for measuring the survival cell count of a probiotic strain at the completion of the guarantee period and for setting the guaranteed cell count, to carry out a long term storage test to be comparable to the guarantee period. Thus, it takes time to supply probiotic products in the market.

Therefore, in order to shorten the storage test of probiotic products, techniques for performing an accelerated test at a high storage temperature to thereby estimate the survival cell count using the result of the accelerated test, are being studied (refer to Non-patent Documents 1 to 4).

However, since the storage temperature has to be set high so as to shorten the span of the accelerated test and such a high temperature leads to an increase in the bacterial inactivation rate, it is very difficult for this test to accurately estimate the survivability at a normal storage temperature. Moreover, if the set temperature of the accelerated test is slightly higher than normal temperature, it is not possible to sufficiently shorten the span of the storage test.

Incidentally, it is known that the survivability of bifidobacteria changes depending on the moisture content and the water activity value of the product (refer to Non-patent Document 5). Furthermore, it is known that the survivability of bifidobacteria changes depending not only on the water activity value of the product but also on the storage temperature of the product (refer to Non-patent Document 6). In addition, it is known that bifidobacteria have different survivabilities per each strain (Non-patent Document 7). Moreover, reportedly, the survivability of lactic acid bacteria also changes depending on the storage temperature and the water activity value (refer to Non-patent Document 8).

[Non-patent Document 1]: Damjanovic, V. and Radulovic, D.), "Cryobiology", (UK), 1968, Vol. 5, p. 101-104
[Non-patent Document 2] Achour et al., "Journal of Chemical Technology and Biotechnology", (UK), 2001, Vol. 76, p. 624-628
[Non-patent Document 3] Ziadi et al., "Biochemical Engineering Journal", (Holland), 2005, Vol. 24, p. 141-145
[Non-patent Document 4] Portner et al. "Cryobiology", (UK), 2007, Vol. 54, p. 265-270
[Non-patent Document 5] Nagawa et al., "Journal of Dairy Science", (USA), 1988, Vol. 71, p. 1777-1782
[Non-patent Document 6] Tatematsu et al. "Japanese Journal of Freezing and Drying", 1982, Vol. 28, p. 40-45
[Non-patent Document 7] Simpson et al., "Journal of Applied Microbiology", (UK), 2005, Vol. 99, p. 493-501
[Non-patent Document 8] Higl et al., "Biotechnology Progress", (US), 2007, Vol. 23, p. 794-800

DISCLOSURE OF THE INVENTION

Problems to be Solved by the Invention

However, these Non-patent Documents 5 to 8 have not led to the idea of analyzing the correlation between the storage temperature and the water activity value and estimating the survival cell count in the product on the basis of the correlation therebetween.

The present invention addresses the above-mentioned situation, with an object of providing a method for estimating survival cell count, which is able to calculate an accurately estimated result of the survival cell count of a specific strain in a probiotic product with respect to its storage period, and to shorten the time for developing the product, and a method for setting a guaranteed cell count, which is able to readily calculate a guaranteed cell count of a specific strain in a probiotic product within its quality guarantee period.

Means for Solving the Problems

The inventors of the present invention discovered that the survival cell count of a specific strain belonging to bifidobacteria, lactic acid bacteria, and the like, contained in a composition after storage is dependent on the storage temperature of the composition and the water activity value of the composition, and that there is a correlation between the common logarithmic value of the survival cell count and the storage period. Then, a regression coefficient derived from the correlation was defined as the bacterial inactivation rate. It was also discovered that the inactivation rate changes depending on the water activity value, and that the natural logarithmic value of the inactivation rate shows a positive correlation with the water activity value. Moreover, it was also discovered that the inactivation rate follows the Arrhenius Law and has a correlation with the storage temperature, and that inactivation rate constant and constants of regression lines derived from the relation between the inactivation rate and the water activity value have strong correlations with the storage temperature. Then, using the correlations among the inactivation rate, the storage temperature, and the water activity value, a relation equation regarding the bacterial inactivation rate and the survival cell count (CFU/g) of a specific strain was completed. Therefore, it was made possible for the method for estimating survival cell count to calculate and output an accurately estimated result of the survival cell count (CFU/g), by substituting input values of a viable cell count at the initiation of storage, a storage temperature (° C.), a water activity value, and a storage period (days) into this relation equation. Furthermore, it was also made possible for the method for setting guaranteed cell count to calculate and output a result of the guaranteed cell count (CFU/g) of a probiotic product within a guarantee period (days) when stored at or under a specified temperature (° C.), by using the survival cell count (CFU/g) derived from the relation equation.

In order to achieve the above object, the present invention employed the following aspects.

(1) A method for estimating survival cell count which estimates a survival cell count $n_t$(CFU/g) of a specific strain contained in a composition after storage by the following equation (I), $$\mathrm{Log}_{10} n_t = \mathrm{Log}_{10} n_0 - t \times \mathrm{EXP}\{(A_T \times T + B_T)w + (C_T \times T + D_T)\} \quad (I)$$

t: storage period (days)×1/30

$n_t$: survival cell count (CFU/g) of the strain contained in the composition after the storage period t (days)

$n_0$: viable cell count (CFU/g) of the strain contained in the composition at the initiation of storage T: storage temperature (° C.)

w: water activity value of the composition $A_T$: experimentally determined coefficient specific to the strain $B_T$: experimentally determined constant specific to the strain $C_T$: experimentally determined coefficient specific to the strain $D_T$: experimentally determined constant specific to the strain.

(2) The method for estimating survival cell count according to (1), wherein the strain is classified into bifidobacteria or lactic acid bacteria.

(3) The method for estimating survival cell count according to (2), wherein the strain is a *bifidobacterium* selected from any one of *Bifidobacterium longum*, *Bifidobacterium breve*, and *Bifidobacterium pseudolongum*.

(4) The method for estimating survival cell count according to (2), wherein
the stain is *Bifidobacterium longum* ATCC BAA-999.

(5) The method for estimating survival cell count according to (2), wherein
the strain is *Bifidobacterium breve* BCCM LMG 23729.

(6) The method for estimating survival cell count according to (2), wherein
the strain is *Bifidobacterium psuedolongum* IFO 15861.

(7) The method for estimating survival cell count according to (2), wherein the stain is a lactic acid bacterium selected from *Lactobacillus gasseri*, *Lactobacillus acidophilus*, *Lactobacillus rhamnosus*, *Lactobacillus plantrum*, and *Enterococcus faecium*.

(8) The method for estimating survival cell count according to (2), wherein
the strain is *Lactobacillus acidophilus* IFO-15862 (*Lactobacillus acidophilus* LAC-300).

(9) The method for estimating survival cell count according to any one of (1) to (8), wherein the water activity value w is less than or equal to 0.6.

(10) The method for estimating survival cell count according to any one of (1) to (9), wherein the storage temperature T(° C.) is 25° C. to 60° C.

(11) A method for setting a guaranteed cell count is characterized by calculating the guaranteed cell count N(CFU/g) within a guarantee period t'(days) when stored at or under the storage temperature T'(° C.) by the following equation (II), $$N = n_t' \times a \quad (II)$$

$n_t'$: survival cell count $n_t$ (CFU/g) of the strain contained in the composition after a storage period t (days), which has been estimated by the method for estimating the survival cell count according to any of (1) to (9), assuming that the storage temperature T (° C.) is T' (° C.) and the storage period t (days) is a guarantee period t' (days)

a: constant less than 1.

Effect of the Invention

According to the method for estimating survival cell count of the present invention, it is possible to calculate an accurately estimated result of the survival cell count (CFU/g) of a specific strain in a probiotic product with respect to its storage period, and to shorten the time for developing the product.

According to the method for setting a guaranteed cell count of the present invention, it is possible to readily calculate a guaranteed cell count of a specific strain in a probiotic product within its quality guarantee period.

BEST MODE FOR CARRYING OUT THE INVENTION

Figure 1:
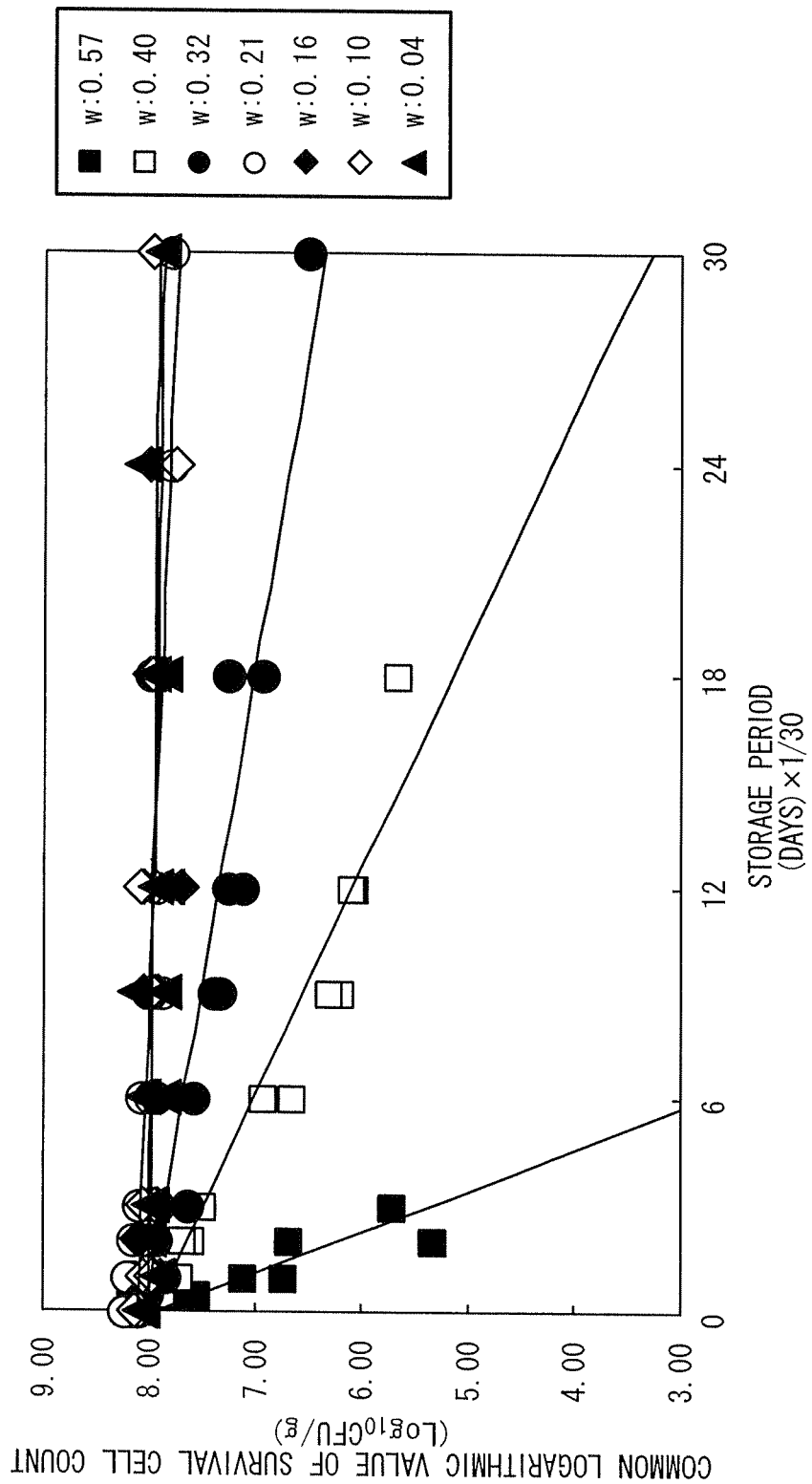
FIG. 1 is a graph showing the survival cell count of *B. longum* BAA-999 at a storage temperature of 25° C.

A method for estimating survival cell count of the present invention calculates and outputs an estimated result of the survival cell count $n_t$ (CFU/g) of a specific strain contained in a composition after storage, in accordance with the following equation (I).

$$\text{Log}_{10} n_t = \text{Log}_{10} n_0 - t \times \text{EXP}\{(A_T \times T + B_T)w + (C_T \times T + D_T)\} \tag{I}$$

t: storage period (days)×1/30

$n_t$: survival cell count (CFU/g) of the strain contained in the composition after the storage period t (days)

$n_0$: viable cell count (CFU/g) of the strain contained in the composition at the initiation of storage T: storage temperature (° C.)

w: water activity value of the composition $A_T$: experimentally determined coefficient specific to the strain $B_T$: experimentally determined constant specific to the strain $C_T$: experimentally determined coefficient specific to the strain $D_T$: experimentally determined constant specific to the strain The "specific strain" is not specifically limited, although preferred subject is a probiotic strain contained in a composition. The term "probiotic" refer to a bacterium which confers a beneficial effect on the human or animal health by acting as a good bacterium inside the intestine when administered alive into the host human or animal.

The strains being the object of the method for estimating the survival cell count of the present invention is bifidobacteria such as *Bifidobacterium longum*, *Bifidobacterium breve*, *Bifidobacterium pseudolongum*, and *Bifidobacterium infantis*. The bifidobacteria (the genus *Bifidobacterium*) is a kind of obligate anaerobic bacteria particularly found a lot in human infant intestines or the like and used as a probiotic for various applications.

Specific examples of the strain belonging to bifidobacteria can include *Bifidobacterium longum* ATCC BAA-999 (product name: *Bifidobacterium longum* BB536, manufactured by Morinaga Milk Industry Co., Ltd), *Bifidobacterium breve* BCCM (BCCM: Belgian Co-Ordinated Collections of Micro-organisms) LMG 23729 (product name: *Bifidobacterium breve* M16V, manufactured by Morinaga Milk Industry Co., Ltd), and *Bifidobacterium pseudolongum* IFO 15861 (product name: *Bifidobacterium pseudolongum* M-602, manufactured by Morinaga Milk Industry Co., Ltd). All of them are stably available probiotic strains.

Moreover, the strains being the object of the method for estimating the survival cell count of the present invention is lactic acid bacteria such as *Lactobacillus gasseri*, *Lactobacillus acidophilus*, *Lactobacillus rhamnosus*, *Lactobacillus plantrum*, and *Enterococcus faecium*. The lactic acid bacteria (the genus *Lactobacillus* and the genus *Enterococcus*) are kinds of facultative anaerobic bacteria found in human intestines, fermented milk, or the like, and used as probiotics for various applications Specific examples of the strain belonging to lactic acid bacteria can include *Lactobacillus gasseri* LAC343 (manufactured by Morinaga Milk Industry Co., Ltd), *Lactobacillus acidophilus* LAC361 (manufactured by Morinaga Milk Industry Co., Ltd), *Lactobacillus acidophilus* LAC-300 (manufactured by Morinaga Milk Industry Co., Ltd), *Lactobacillus rhamnosus* LCS742 (manufactured by Morinaga Milk Industry Co., Ltd), *Lactobacillus plantrum* LP83 (manufactured by Morinaga Milk Industry Co., Ltd), *Enterococcus faecium* FA5 (manufactured by Morinaga Milk Industry Co., Ltd), and such lactic acid bacteria. All of them are stably available probiotic strains.

The strains being the object of the method for estimating the survival cell count of the present invention can be applied to compositions such as food products including health foods, confectioneries (cream, cream-filled sandwich cookies, chocolate, chocolate flakes, breakfast cereals, gum, and the like), and baby milk powder, as well as to pharmaceuticals, livestock foods, and drugs. The form of the composition is not specifically limited, but compositions which stay in a solid state during storage are targeted. Examples thereof can include powder, powder-containing capsules, and tablets containing compressed powder with an excipient.

Moreover, the composition being the object of the method for estimating the survival cell count of the present invention needs to be sealed up in a moisture barrier container to be applicable to the method for estimating the survival cell count. If the composition is not sealed up in a moisture barrier container, the water activity value w may possibly change from the initiation time of storage with the passage of storage period, which may make it difficult to accurately estimate the survival cell count $n_t$ (CFU/g) with respect to the storage period by the method for estimating the survival cell count of the present invention.

Furthermore, the composition being the object of the method for estimating the survival cell count of the present invention also needs to be contained in a light blocking container during storage. If the composition is contained in a container having an insufficient-light blocking property, the survival cell count $n_t$ (CFU/g) of a strain may decrease due to ultraviolet radiation, which may make it difficult to accurately estimate the survival cell count $n_t$ (CFU/g) with respect to the storage period by the method for estimating the survival cell count of the present invention.

The symbol t in the above-mentioned equation (I) refers to a value obtained by multiplying the storage period (days) by 1/30, and corresponds to the storage period per month when one month is assumed to be 30 days.

Preferably, the storage period t (days) is supposed to be 1 to 1,500 days. Within this range, the survival cell count $n_t$ (CFU/g) of the strain contained in the composition after the storage period t (days) can be more accurately estimated by the method for estimating the survival cell count of the present invention.

The symbol $n_t$ refers to a survival cell count $n_t$ (CFU/g) of a specific strain contained in a composition after a storage period t (days) estimated by the above-mentioned equation (I). The value $n_t$ can be calculated by substituting the storage period t (days), a viable cell count $n_0$ (CFU/g) of the strain contained in the composition at the initiation of storage, a storage temperature T (° C.), experimentally determined strain-specific coefficients $A_T$ and $C_T$, experimentally determined strain-specific constants $B_T$ and $D_T$, and the water activity value w of the composition, into the above-mentioned equation (I).

The symbol $n_0$ refers to a viable cell count (CFU/g) of the strain contained in the composition at the initiation of storage. If the production time is regarded as the initiation time of storage, the value $n_0$ is supposed to be equal to the viable cell count (CFU/g) of the specific strain when added to the composition during the production time of the composition containing the specific strain.

The symbol T (° C.) refers to the storage temperature (° C.), that is, the temperature for storing the composition. The above-mentioned equation (I) is to estimate the survival cell count $n_t$ (CFU/g) based on the assumption that the storage temperature T (° C.) is fixed throughout the storage period of the composition.

In addition, the set value of the storage temperature T (° C.) is not specifically limited, although it is preferable to set from 25 to 60° C. If the storage temperature T (° C.) is from 25 to 60° C., a strong correlation can be found between the survival cell count $n_t$ (CFU/g) of the specific strain contained in the composition and the storage temperature T (° C.), making it possible to more accurately estimate the survival cell count $n_t$ (CFU/g) of the specific strain contained in the composition.

The symbol w refers to the water activity value of the composition. The water activity value means a value defined as the ratio of the water vapor pressure (P) inside a sealed container enclosing an analyte to the water vapor pressure (PO) of pure water (P/PO, provided that P and PO are water vapor pressures under the same temperature condition). It is a scale of the content of non-combined water, that is, free water, contained in the analyte, and is mostly used as an index to indicate the bacterial growth potential. The water activity value is expressed in a range from 0.000 to 1.000. The water activity of pure water is 1.000, and the water activity of dried food is shown to be about 0.6 or less.

The water activity value w of the composition is set at the stage for producing the composition. The water activity value w can be set, for example, by a method in which compositions having a variety of water activity values w are mixed at predetermined proportions to achieve a desired water activity value w, a method in which salt, sugar, or the like, is dissolved in a composition to thereby reduce the free water content, and a method in which a composition is dried or moistened with water. The above-mentioned equation (I) is to estimate the survival cell count $n_t$ (CFU/g) based on the assumption that the water activity value w is fixed throughout the storage period.

The set value of the water activity value w is not specifically limited, although it is preferable to set within 0.6, and more preferably from 0.10 to 0.40. If the water activity value w is within 0.6, a strong correlation can be found between the survival cell count $n_t$ (CFU/g) of the specific strain contained in the composition and the water activity value w, making it possible to more accurately estimate the survival cell count $n_t$ (CFU/g) of the specific strain contained in the composition.

The symbols $A_T$, $B_T$, $C_T$, and $D_T$ refer to coefficients or constants specific to a strain determined by the following experiment 1) to 5).

1) The target specific strain is respectively added to powdery compositions having at least three different water activity values w and evenly mixed to thereby produce specific strain-containing composition samples. Each sample is then individually packed and sealed up in a plural number of (number of storage temperature conditions×number of storage period conditions) moisture barrier containers, by which a plurality of sealed samples are given per each water activity value w. Then, each sealed sample is stored in at least three different storage temperatures (° C.). Thereafter, the survival cell count $n_t$ (CFU/g) in the composition is measured at least three time points within the storage period (days).

2) The survival cell counts $n_t$ (CFU/g) within the storage period are plotted by having the common logarithmic value of the survival cell count $n_t$ (CFU/g) of the specific strain in the respective samples which have undergone different storage conditions (storage temperature (° C.) and water activity value) on the Y-axis and the storage period t (days)×1/30 on the X-axis. Furthermore, the regression line of respective storage condition is calculated using these plots, and the slope of the regression line of respective storage condition (regression coefficient) is defined as the inactivation rate.

3) Next, by having the natural logarithmic value of the inactivation rate at respective storage temperature (° C.) on the Y-axis and the water activity value w on the X-axis, the relation between both parties is plotted. Using this plot, the regression line (y=ax+b) of respective storage temperature (° C.) is respectively calculated.

4) By having the slope (a) of the linear equation of respective storage temperature (° C.) obtained from the step 3) on the Y-axis and the storage temperature T (° C.) on the X-axis, the relation between both parties is plotted. Using this plot, a linear equation is obtained, and the slope $A_T$ and the Y-intercept $B_T$ of the resultant regression line are calculated.

5) Moreover, by having the constant (b) of the regression line obtained from the step 3) on the Y-axis and the storage temperature T (° C.) on the X-axis, the relation between both parties is plotted. A linear equation thereof is obtained, and the slope $C_T$ and the Y-intercept $D_T$ of the resultant linear equation are calculated.

Here, in the step 2), it is found from the relation between the storage period and the survival cell count $n_t$ (CFU/g) obtained from the step 1), that the survival cell count $n_t$ (CFU/g) rapidly decreases from the initiation of storage of the sample but the decrease of the survival cell count $n_t$ (CFU/g) is gradually decelerated with the passage of storage period. For this reason, the relation with between the time and the survival cell count $n_t$ (CFU/g) of the specific strain can be expressed by a linear equation (regression line). The slope of the regression line (regression coefficient) represents the common logarithmic value of the count of killed bacteria per month of storage period, and this regression coefficient is defined as the inactivation rate in the present invention. This inactivation rate is different per each setting of the storage temperature and the water activity value w. As the water activity value w or the storage temperature gets higher, a higher inactivation rate is shown.

After the regression linear equations (y=ax+b) of the respective storage temperatures have been calculated in the step 3), relations between the slopes (a) of these plurality of regression linear equations (corresponding to the inactivation rate constant k' of a specific strain contained in a composition that will be described later in detail in the test example 1) and the storage temperatures of the respective equations are plotted so as to obtain the linear equation (k'=$A_T$×T+$B_T$), from which the slope $A_T$ serving as the coefficient of the linear equation and the Y-intercept $B_T$ serving as the constant of the linear equation is calculated in the step 4).

Moreover, relations between the constants (b) of the plurality of regression linear equations (corresponding to the constant C regarding the inactivation rate of the specific strain contained in the composition that will be described later in detail in the test example 1) and the storage temperatures of the respective equations are plotted so as to obtain the linear equation (C=$C_T$×T+$D_T$), from which the slope $C_T$ serving as the coefficient of the linear equation and the Y-intercept $D_T$ serving as the constant of the linear equation is calculated in the step 5).

The equation (I) of each specific strain can be derived by substituting these values $A_T$, $B_T$, $C_T$, and $D_T$, which have been determined per each specific strain from the experiment 1) to 5) in the above-mentioned manner, into the aforementioned equation (I).

The form of the specific strain for use in a sample in the step 1) can be exemplified by a bacterial powder or a liquid, although preferred is a bacterial powder. This is because that: a specific strain is usually supplied in a form of bacterial powder; the state of bacterial powder is easy to evenly mix with a powdery composition; and furthermore, it is not likely to change the water activity value w of a powdery composition whose water activity value w has been pre-adjusted, only by adding a small amount of bacterial powder to the powdery composition.

The water activity value w of the powdery composition for use in the sample is preferably from 0.05 to 0.60. The reason is that: this is a usual range of the water activity value for probiotic products; and within this range, a strong correlation can be found between the water activity value w and the survival cell count $n_t$ (CFU/g) of a strain, making it possible to more accurately estimate the survival cell count $n_t$ (CFU/g) of the powdery composition.

The powdery composition for use in the sample is not specifically limited, and can be exemplified by raw starch such as corn starch, and powder milk.

The water activity value w of the sample can be adjusted by, for example, appropriately mixing raw starch and dry starch so that the powdery composition can have a desired water activity value w.

As described above, the number of kinds of water activity values w for samples is at least three, although it is preferable to employ four or more kinds.

It is necessary to prepare the same number of pieces of samples having a predetermined water activity value was the number of kinds of respective storage temperatures (at least three kinds) and the number of measurements (at least three time points) of the survival cell count $n_t$ (CFU/g) within a predetermined storage period. Therefore, it is necessary to prepare at least nine pieces of individually packed samples for each water activity value, and, appropriately, a necessary number of pieces of samples are individually packed according to the number of kinds of respective storage temperatures and the number of measurements within a predetermined storage period. In this experiment, since at least three kinds of samples having different water activity values w are stored, the total number of sample pieces for use in the experiment is at least twenty seven.

As described above, the container used for the individual packing of the sample needs to have a moisture barrier property. This is to avoid a change in the water activity value w of the sample throughout the storage period so as to achieve more accurate estimation of the survival cell count $n_t$ (CFU/g). Regarding the form of the container having a moisture barrier property, it is possible to employ a sealable bag having a moisture barrier property, a container consisting of a glass or metal jar and a moisture barrier stopper, and the like.

As described above, the number of kinds of storage temperatures T (° C.) for samples is at least three, although it is preferable to set four or more kinds.

The storage temperature T (° C.) for the samples is preferably set from 5 to 60° C. The reason is that: this temperature range is suitable for storing probiotic products; and within this range, a strong correlation can be found between the storage temperature (° C.) and the survival cell count $n_t$ (CFU/g) of a specific strain, making it possible to more accurately estimate the survival cell count $n_t$ (CFU/g).

It is preferable to store the sample by leaving it still in a storage device which can maintain a fixed storage temperature (° C.), such as an incubator and a thermostat bath. The relative humidity with respect to the temperature in the storage device may be let as it is without a specific setting, or may be controlled if necessary.

The measurement of the survival cell count $n_t$ (CFU/g) in the sample is performed at least three time points within the storage period (days), although it is preferable to set four or more time points.

The time for measuring the survival cell count $n_t$ (CFU/g) in the sample is preferably set 1 to 1,500 days after the initiation of storage. It becomes possible, by measuring the survival cell count $n_t$ (CFU/g) in the sample 1 to 1,500 days after the initiation of storage, to more accurately understand the correlation of the storage temperature (° C.) and the water activity value w with respect to the storage period.

For the measurement of the survival cell count $n_t$ (CFU/g) in the sample, it is necessary to appropriately carry out the culture and the measurement by considering whether anaerobic or aerobic the specific strain is. For example, if the specific strain belongs to anaerobic bacteria such as bifidobacteria and lactic acid bacteria, the survival cell count $n_t$ (CFU/g) in the sample is to be measured by the following procedure. First, a sample taken out from a container is diluted with a prescribed buffer solution, and a preset amount of the diluted solution containing the strain is transferred into a Petri dish. A melt agar medium is poured into this Petri dish, and the diluted solution containing the strain and the agar medium are evenly mixed to prepare for pour plate culture. After the agar medium has been solidified, the Petri dish is set in an anaerobic incubator and is subjected to standing culture at a predetermined temperature (36 to 38° C.) for a predetermined period of time (about two to four days). Then, the Petri dish is taken out from the anaerobic incubator, and the number of colonies in the medium is counted to calculate the survival cell count $n_t$ (CFU/g).

According to the method for estimating survival cell count of the present invention, it is possible to calculate and output an estimated result of the survival cell count $n_t$ (CFU/g) of a specific strain after a storage period t (days), by substituting input values of a viable cell count $n_0$ (CFU/g) of the strain contained in the composition at the initiation of storage, a storage temperature T (° C.), a storage period t (days), and a water activity value w, into the above-mentioned equation (I) thus derived per each specific strain.

In this way, by deriving the equation (I) of each specific strain in advance, it becomes possible, in the development of a probiotic product containing a specific strain, to obtain an accurately estimated result of the survival cell count $n_t$ (CFU/g) of the specific strain after a storage period t (days), in accordance with the equation (I) of each specific strain, without performing a storage test. Therefore, the time for developing the probiotic product can be shortened.

In addition, when it comes to the modification of the formulation of a probiotic product, if the water activity value after the modification of the formulation of this product is known, it is possible to obtain an accurately estimated result of the survival cell count $n_t$ (CFU/g) without performing a storage test, by using the method for estimating survival cell count of the present invention. Therefore, the time for developing the product can be shortened.

Moreover, even though the strain in the product is changed, by deriving the equation (I) of each specific strain in advance, it is possible to obtain an accurately estimated result of the survival cell count $n_t$ (CFU/g) without performing a storage test per each change of the strain, by using the respective equation (I) for the concerned specific strain, with the device for estimating survival cell count of the present invention. Therefore, the time for developing the product can be shortened.

Furthermore, with the above-mentioned equation (I), the viable cell count $n_0$ (CFU/g) of a specific strain required for the composition at the initiation of storage can be derived by calculating a survival cell count $n_t$ (CFU/g) after a storage period t (days), a storage temperature T (° C.), the storage period t (days), and a water activity value w.

Similarly, with the above-mentioned equation (I), the storage temperature T (° C.) required for storing a composition can be derived by calculating a viable cell count $n_0$ (CFU/g) of a specific strain contained in the composition at the initiation of storage, a survival cell count $n_t$ (CFU/g) after a storage period t (days), the storage period t (days), and a water activity value w.

Yet, similarly, with the above-mentioned equation (I), the storage period t (days) of a composition can be derived by calculating a viable cell count $n_0$ (CFU/g) of a specific strain contained in the composition at the initiation of storage, a survival cell count $n_t$ (CFU/g) after the storage period t (days), a storage temperature T (° C.), and a water activity value w.

By the method for estimating survival cell count represented by the above-mentioned equation (I), it is also possible to calculate the guaranteed cell count N (CFU/g) of a specific strain contained in a probiotic product by estimating the survival cell count $n_t$ (CFU/g) of the strain contained in the composition after a storage period t (days), in the following manner.

That is, the method for setting a guaranteed cell count of the present invention can calculate the guaranteed cell count N(CFU/g) within a guarantee period t' (days) when stored at or under a temperature T' (° C.), in accordance with the following equation (II).

$$N = n_t' \times a \quad (II)$$

Here, the symbol $n_t'$ refers to the survival cell count $n_t$ (CFU/g) of the strain contained in the composition after a storage period t (days) which has been estimated by the method for estimating a survival cell count represented by the above-mentioned equation (I), assuming that the storage temperature T (° C.) is T' (° C.) and the storage period t (days) is a guarantee period t' (days).

Moreover, the symbol T' (° C.) refers to a specified temperature for storing the probiotic product.

The symbol a refers to a constant less than 1. The constant a is appropriately determined by considering the possibility in which the estimated survival cell count $n_t$ (CFU/g) of a specific strain and the actual survival cell count $n_t$ (CFU/g) may be different due to a change in the storage temperature T (° C.) during the storage period, and is typically set from 0.5 to 0.9.

In this way, the method for setting a guaranteed cell count of the present invention is capable of deriving the guaranteed cell count N(CFU/g) of a specific strain contained in a probiotic product within a quality guarantee period, when stored at or under a temperature T' (° C.), in accordance with the above-mentioned equation (II).

Hereunder is a more detailed description of the method for deriving the above-mentioned equations (I) used in the method for estimating survival cell count of the present invention and the method for setting guaranteed cell count, with reference to test examples.

Test example 1

Test with *Bifidobacterium longum* ATCC BAA-999

Methods

A bacterial powder of *Bifidobacterium longum* ATCC BAA-999 (*Bifidobacterium longum* BB536, manufactured by Morinaga Milk Industry Co., Ltd; hereunder, abbreviated as *B. longum* BAA-999) was used as a test bacterium for this test. Moreover, in order to produce powders having different water activity values w, a raw starch (corn starch having a water activity value of 0.6, manufactured by Nihon Shokuhin Kako Co., Ltd.) and a dry starch (purified and sterilized dry corn starch having a water activity value of 0.02, manufactured by Matsutani Chemical Industry Co., Ltd.) were mixed at various ratios, and thereby seven kinds of raw starches having different water activity values (w=0.04, 0.10, 0.16, 0.21, 0.32, 0.40, and 0.57) were respectively produced.

Next, each of these seven kinds of raw starches was respectively added with about 0.1 mass % of the bacterial powder of *B. longum* BAA-999 at the concentration of $1 \times 10^8$ (CFU/g), and evenly mixed to thereby produce a mixed powder sample of the *B. longum* BAA-999 bacterial powder and the raw starch.

Then, forty moisture barrier aluminum pouches (made of a PET/AL/PE three layered lamination film) were prepared per sample. Then, 2 to 3 g of the sample was individually packed in each aluminum pouch and sealed up by heat sealing. Two to nineteen pouches per sample were placed respectively in four thermostat baths (manufactured by SANYO Electric Co., Ltd.) whose temperature was set at 25° C., 37° C., 45° C., and 60° C., respectively (relative humidity was let as it was) to initiate the storage. Thereafter, each individually packed sample in the aluminum pouch was taken out serially from the thermostat, and the survival cell count was measured respectively. Here, Table 1 shows the number of measurements of the survival cell count $n_t$ (CFU/g) in each sample with respect to the storage period (days) at the storage temperature of 25° C. Table 2 shows the number of measurements of the survival cell count $n_t$ (CFU/g) in each sample with respect to the storage period (days) at the storage temperature of 37° C. Table 3 shows the number of measurements of the survival cell count $n_t$ (CFU/g) in each sample with respect to the storage period (days) at the storage temperature of 45° C. Table 4 shows the number of measurements of the survival cell count $n_t$ (CFU/g) in each sample with respect to the storage period (days) at the storage temperature of 60° C. In addition, the survival cell count $n_t$ (CFU/g) was measured by the following procedure 1) to 6).

1) The aluminum pouch of the sample was opened in a clean bench. The sample was taken out from the aluminum pouch, 1 g of which was added into 99 ml of a sterilized suspension buffer ($KH_2PO_4$; 4.5 g, $Na_2PO_4$; 6.0 g, L-cysteine; 0.5 g, Tween-80; 0.5 g, and distilled water; 1,000 ml). At that time, the suspension buffer had been warmed at 30 to 40° C. in advance.

2) The sample was completely eluted in the suspension buffer to produce a suspended solution.

3) This suspended solution was diluted with 9.9 ml of a sterilized physiological saline in accordance with a usual method, to produce a diluted solution.

4) This diluted solution was dispensed at 0.1 to 1.0 ml in each Petri dish using a pipette. Then, about 20 ml of a melt BL agar medium at 45 to 50° C. (blood-free medium, manufactured by Nikken Chemical Laboratory Co., Ltd. or Nippon Suisan Kaisha, Ltd.) was poured into the Petri dish containing the dispensed diluted solution, and the diluted solution was mixed with the BL agar medium to prepare for pour plate culture.

5) After the BL agar medium had been solidified, the Petri dish was taken out from the clean bench, and as immediately as possible set in an anaerobic incubator filled with a mixed gas ($N_2$; 80%, $CO_2$; 10%, and $H_2$; 10%), followed by a standing culture of the surviving bacterium in the sample at 37° C. for three days under the anaerobic condition.

6) After the three day culture, the Petri dish was taken out from the anaerobic incubator, and the number of colonies formed in the BL agar medium was counted to thereby obtain the survival cell count $n_t$ per gram of powder (CFU/g) in accordance with a usual method.

TABLE 1

Number of measurements of survival cell count in each sample with respect to storage period (days) at storage temperature of 25° C.

| Storage period (days) | W: 0.57 | W: 0.40 | W: 0.32 | W: 0.21 | W: 0.16 | W: 0.10 | W: 0.04 |
|---|---|---|---|---|---|---|---|
| 0 | 2 | 2 | 2 | 2 | 2 | 2 | 2 |
| 14 | 2 | 2 | 2 | 1 | 1 | 0 | 0 |
| 30 | 2 | 2 | 2 | 2 | 2 | 2 | 1 |
| 60 | 2 | 2 | 2 | 2 | 2 | 0 | 1 |
| 90 | 1 | 1 | 2 | 1 | 2 | 2 | 2 |
| 180 | 0 | 2 | 2 | 2 | 2 | 2 | 2 |
| 270 | 0 | 2 | 2 | 2 | 2 | 2 | 2 |
| 360 | 0 | 2 | 2 | 2 | 2 | 2 | 2 |
| 540 | 0 | 1 | 2 | 2 | 2 | 2 | 2 |
| 720 | 0 | 0 | 0 | 1 | 1 | 1 | 1 |
| 900 | 0 | 0 | 1 | 1 | 0 | 1 | 1 |
| Total number of measurements | 9 | 16 | 19 | 18 | 18 | 16 | 16 |

TABLE 2

Number of measurements of survival cell count in each sample with respect to storage period (days) at storage temperature of 37° C.

| Storage period (days) | W: 0.57 | W: 0.40 | W: 0.32 | W: 0.21 | W: 0.16 | W: 0.10 | W: 0.04 |
|---|---|---|---|---|---|---|---|
| 0 | 2 | 2 | 2 | 2 | 2 | 2 | 2 |
| 4 | 1 | 1 | 0 | 0 | 0 | 0 | 0 |
| 7 | 2 | 2 | 2 | 0 | 0 | 0 | 0 |
| 10 | 1 | 0 | 0 | 0 | 0 | 0 | 0 |
| 14 | 0 | 2 | 2 | 2 | 1 | 1 | 0 |
| 30 | 0 | 2 | 2 | 2 | 2 | 2 | 0 |
| 60 | 0 | 0 | 2 | 2 | 2 | 0 | 0 |
| 90 | 0 | 0 | 1 | 1 | 2 | 2 | 2 |
| 180 | 0 | 0 | 0 | 2 | 2 | 2 | 2 |
| 270 | 0 | 0 | 0 | 1 | 2 | 2 | 2 |
| 360 | 0 | 0 | 0 | 0 | 2 | 2 | 2 |
| 540 | 0 | 0 | 0 | 0 | 2 | 2 | 2 |
| 720 | 0 | 0 | 0 | 0 | 0 | 1 | 1 |
| 900 | 0 | 0 | 0 | 0 | 0 | 1 | 1 |
| Total number of measurements | 6 | 9 | 11 | 12 | 17 | 17 | 14 |

TABLE 3

Number of measurements of survival cell count in each sample with respect to storage period (days) at storage temperature of 45° C.

| Storage period (days) | W: 0.57 | W: 0.40 | W: 0.32 | W: 0.21 | W: 0.16 | W: 0.10 | W: 0.04 |
|---|---|---|---|---|---|---|---|
| 0 | 2 | 2 | 2 | 2 | 2 | 2 | 2 |
| 2 | 1 | 2 | 2 | 0 | 0 | 0 | 0 |
| 4 | 1 | 2 | 2 | 2 | 2 | 1 | 1 |
| 7 | 0 | 1 | 2 | 2 | 2 | 2 | 1 |
| 14 | 0 | 0 | 2 | 2 | 2 | 2 | 2 |
| 21 | 0 | 0 | 0 | 1 | 0 | 0 | 0 |
| 30 | 0 | 0 | 1 | 2 | 2 | 2 | 2 |
| 60 | 0 | 0 | 0 | 1 | 1 | 2 | 2 |
| 90 | 0 | 0 | 0 | 1 | 1 | 2 | 2 |
| 180 | 0 | 0 | 0 | 1 | 0 | 2 | 2 |
| 270 | 0 | 0 | 0 | 0 | 0 | 2 | 1 |
| 360 | 0 | 0 | 0 | 0 | 0 | 0 | 1 |
| Total number of measurements | 4 | 7 | 11 | 14 | 12 | 17 | 16 |

TABLE 4

Number of measurements of survival cell count in each sample with respect to storage period (days) at storage temperature of 60° C.

| Storage period (days) | W: 0.57 | W: 0.40 | W: 0.32 | W: 0.21 | W: 0.16 | W: 0.10 | W: 0.04 |
|---|---|---|---|---|---|---|---|
| 0 | 2 | 2 | 2 | 2 | 2 | 2 | 2 |
| 1 | 0 | 0 | 0 | 1 | 0 | 0 | 0 |
| 2 | 0 | 1 | 0 | 2 | 2 | 0 | 0 |
| 3 | 0 | 0 | 0 | 1 | 0 | 0 | 0 |
| 4 | 0 | 0 | 0 | 2 | 2 | 2 | 2 |
| 7 | 0 | 0 | 0 | 0 | 2 | 2 | 2 |
| 10 | 0 | 0 | 0 | 0 | 0 | 1 | 0 |
| 14 | 0 | 0 | 0 | 0 | 1 | 2 | 2 |
| 30 | 0 | 0 | 0 | 0 | 0 | 0 | 2 |
| 60 | 0 | 0 | 0 | 0 | 0 | 0 | 2 |
| 90 | 0 | 0 | 0 | 0 | 0 | 0 | 1 |
| Total number of measurements | 2 | 3 | 2 | 8 | 9 | 9 | 13 |

Results

Figure 2:
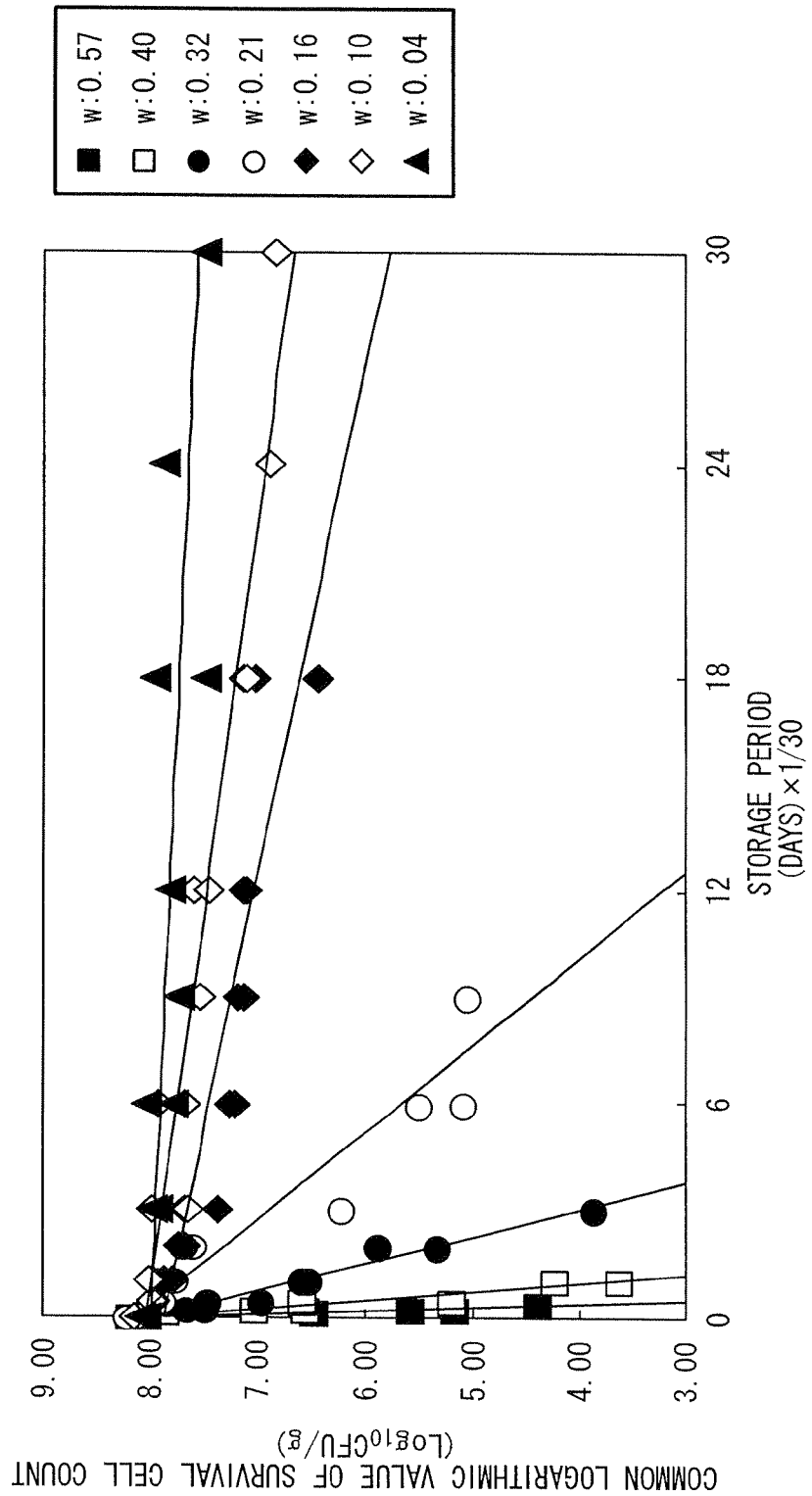
FIG. 2 is a graph showing the survival cell count of *B. longum* BAA-999 at a storage temperature of 37° C.
Figure 3:
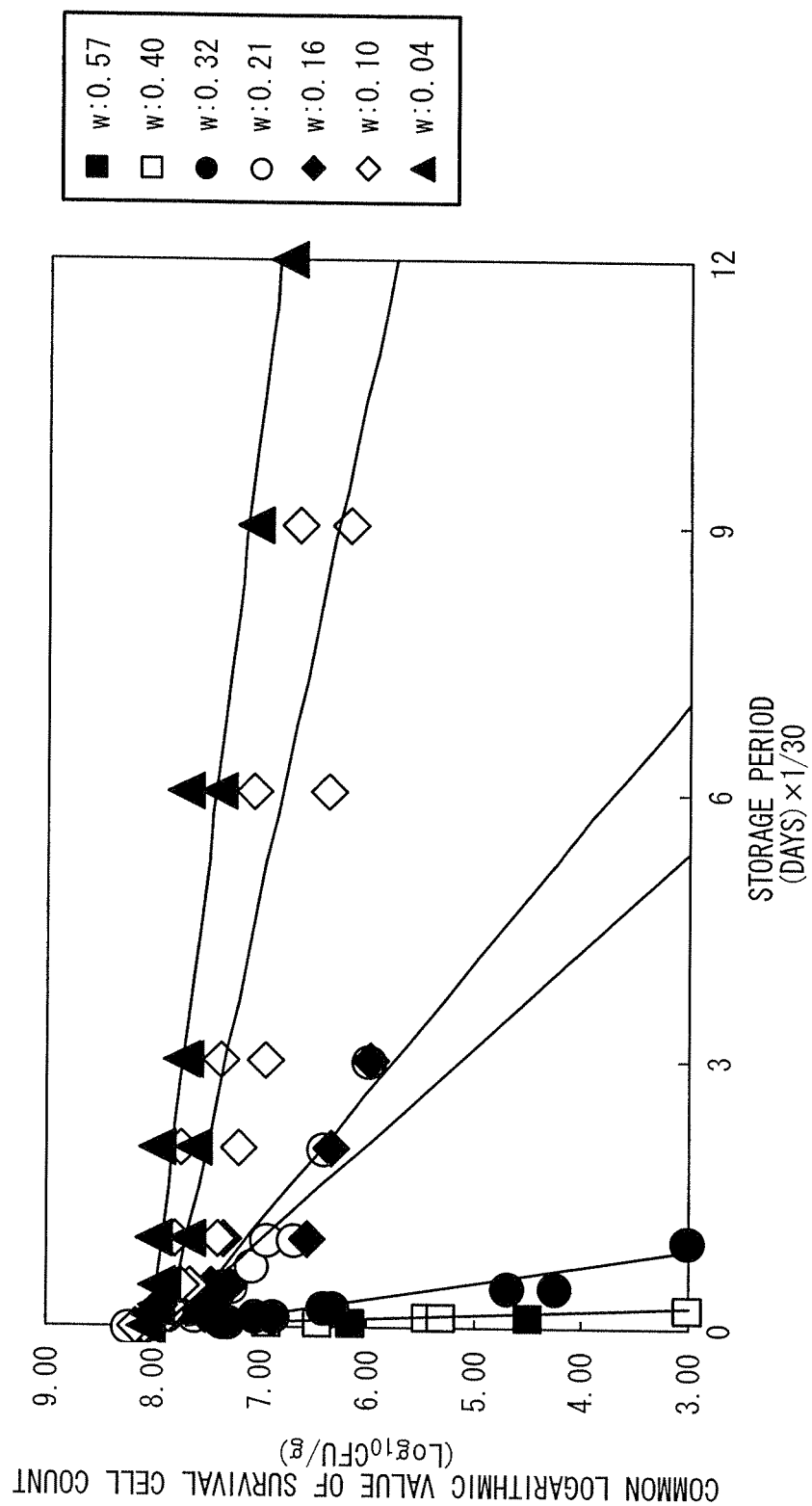
FIG. 3 is a graph showing the survival cell count of *B. longum* BAA-999 at a storage temperature of 45° C.
Figure 4:
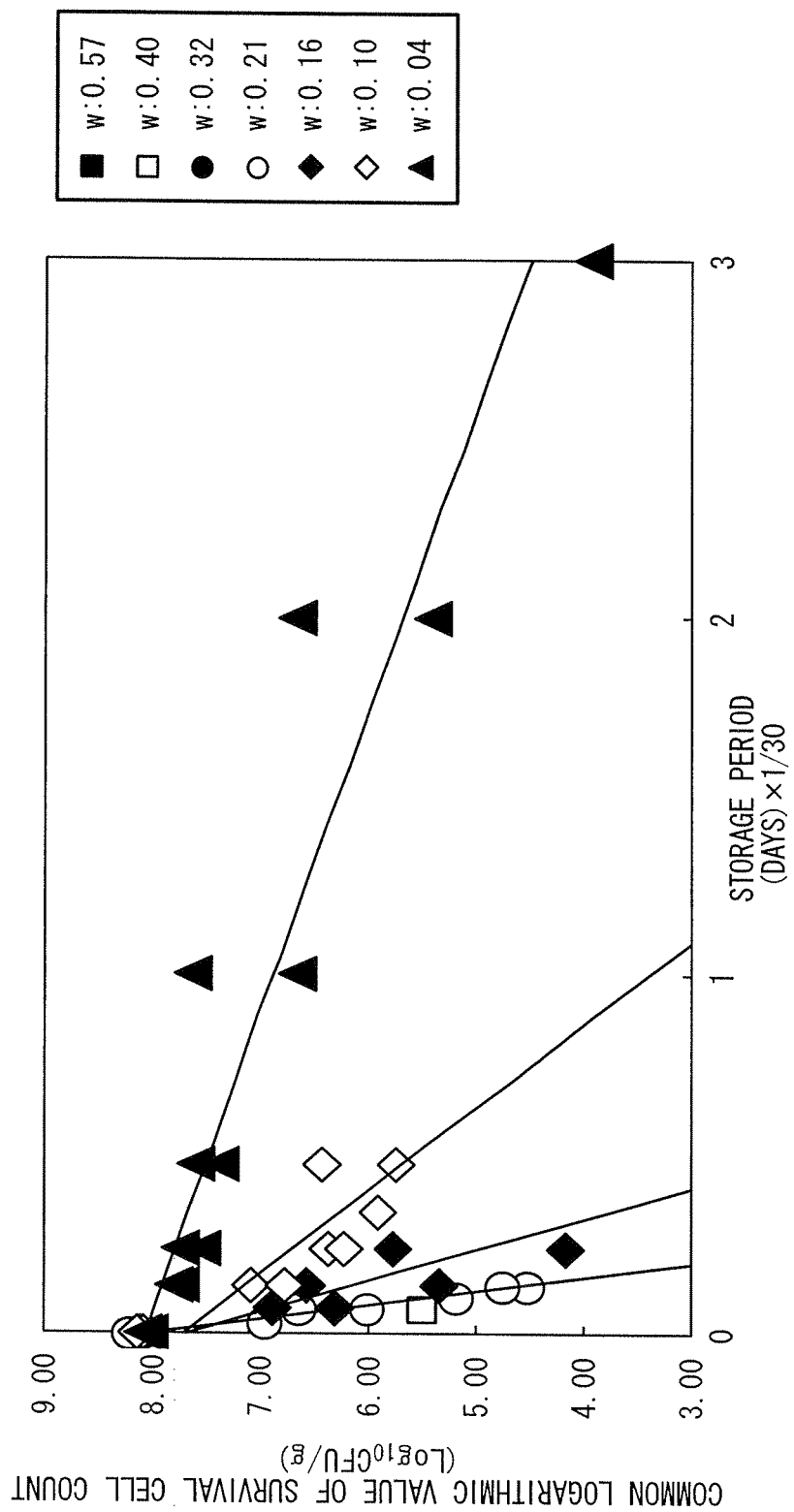
FIG. 4 is a graph showing the survival cell count of *B. longum* BAA-999 at a storage temperature of 60° C.

The thus counted timewise measurement results of the survival cell count $n_t$ (CFU/g) in the respective samples having different water activity values w at the respective storage temperatures (° C.) are shown in FIG. 1 for the case of the storage temperature of 25° C., FIG. 2 for the case of the storage temperature of 37° C., FIG. 3 for the case of the storage temperature of 45° C., and FIG. 4 for the case of the storage temperature of 60° C. In the FIGS. 1 to 4, the X-axis shows the storage period (days)×1/30 and the Y-axis shows the common logarithmic value of the survival cell count ($Log_{10}$ CFU/g).

Next, the regression lines of respective samples were formed from FIGS. 1 to 4. Then, regarding samples which gave highly correlated regression lines ($R^2 > 0.6$), the absolute value of the slope of the regression line was defined as the inactivation rate k of the strain. The following Table 5 shows the inactivation rates k at respective storage temperatures T (° C.) with variations of water activity values w. Here, the unit of the inactivation rate k in Table 5 is $Log_{10}$ CFU/g/month which represents the common logarithmic value of the count of killed bacteria per month. In addition, those exhibiting poor reliability in terms of the inactivation rate k, because of a small number of times of measurement or low correlation of the regression line ($R^2$<0.6), were denoted by N.D.

TABLE 5

| Storage temperature | Water activity value w | | | | | | |
|---|---|---|---|---|---|---|---|
| | 0.57 | 0.4 | 0.32 | 0.21 | 0.16 | 0.1 | 0.04 |
| 60° C. | N.D. | N.D. | N.D. | 26.036 | 11.601 | 4.285 | 1.195 |
| 45° C. | N.D. | 21.509 | 5.361 | 0.913 | 0.681 | 0.176 | 0.099 |
| 37° C. | 11.011 | 4.198 | 1.294 | 0.404 | 0.07 | 0.046 | 0.015 |
| 25° C. | 0.857 | 0.155 | 0.056 | 0.012 | N.D. | N.D. | N.D. |

Here, the survival cell count $n_t$ (CFU/g) of a specific strain after a storage period t (days) can be expressed by the following equation (1), provided that the symbol k stands for the inactivation rate shown in Table 5 and the symbol t stands for the storage period.

$$Log_{10} n_t = Log_{10} n_0 - t \times k \qquad (1)$$

$n_t$: survival cell count $n_t$ (CFU/g) of the strain contained in the composition after the storage period t (days)

$n_0$: viable cell count (CFU/g) of the strain contained in the composition at the initiation of storage t: storage period (days)×1/30 k: inactivation rate ($Log_{10}$ CFU/g/month)

Moreover, the following equation (2) was obtained by modifying the above-mentioned equation (1).

$$k = (N_0 - N_t)/t \qquad (2)$$

Figure 5:
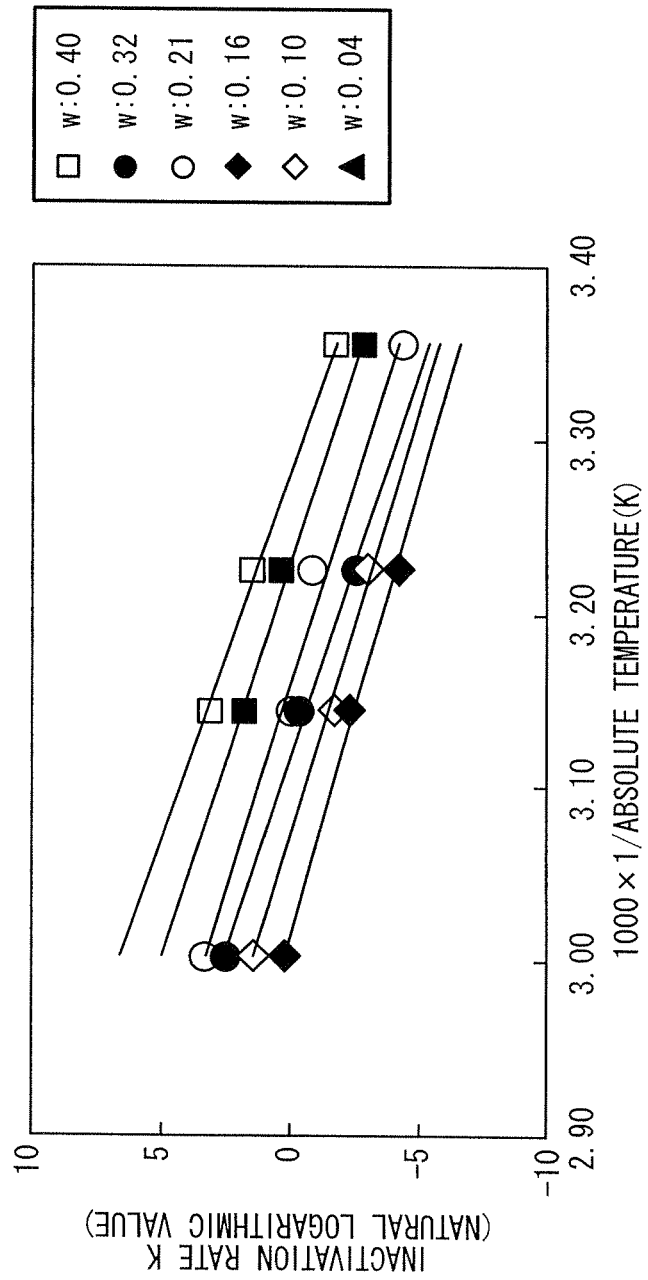
FIG. 5 shows Arrhenius plots of the inactivation rate k of *B. longum* BAA-999.

$N_0$: common logarithmic value of $n_0$, that is, $Log_{10} n_0$ $N_t$: common logarithmic value of $n_t$, that is, $Log_{10} n_t$ On the other hand, the inactivation rate k of Table 5 was converted into the natural logarithmic value, and the inverse number of the absolute temperature (K) of the storage temperature T (° C.) was obtained. Thereafter, the relation between the natural logarithmic value of the inactivation rate k and the inverse number of the absolute temperature (K) was plotted to thereby obtain the regression lines as shown in FIG. 5. These regression lines with the respective water activity values w showed strong negative correlations ($R^2$>0.98) between the inactivation rate k and the inverse number of the absolute temperature (K). Accordingly, it was shown that, with any water activity value w, the inactivation rate k is in a relation depending on the storage temperature T (° C.) (the inactivation rate k increases as the storage temperature T (° C.) increases) following the Arrhenius Law, and that the regression lines of FIG. 5 are Arrhenius plots.

By so doing, it was understood that, when it comes to *B. longum* BAA-999, with any water activity value w, the inactivation rate k is dependent on the storage temperature (° C.), and the natural logarithmic value of the inactivation rate k and the and the storage temperature (° C.) are in a proportional relation.

Figure 6:
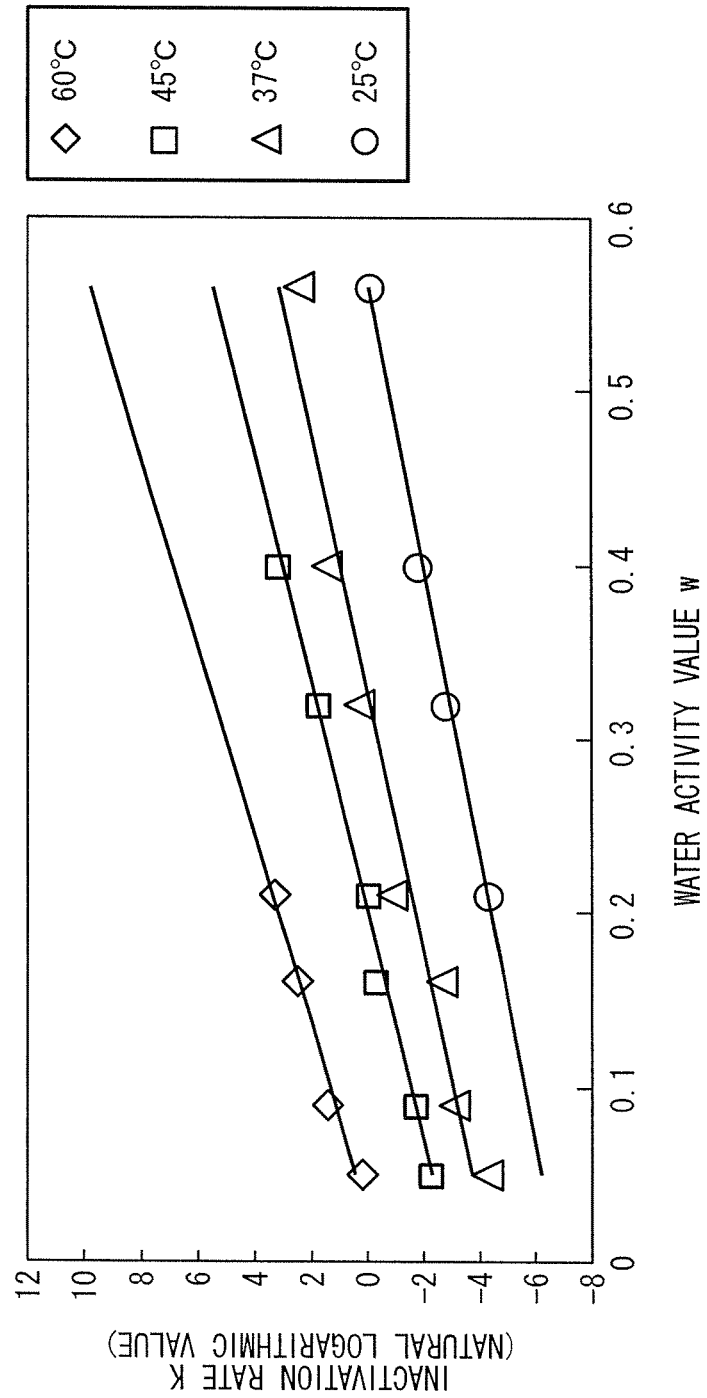
FIG. 6 shows relations between the water activity value w and the inactivation rate k of *B. longum* BAA-999 at respective storage temperatures (° C.).

Moreover, the natural logarithmic value of the inactivation rate k at respective temperature calculated from Table 5 was obtained, after which the relation between the natural logarithmic value of the inactivation rate k at respective storage temperature and the water activity value w of the sample was plotted to thereby obtain the regression lines as shown in FIG. 6. Then, from the correlations of these regression lines, it was revealed that, at any storage temperature (° C.), there was a strong positive correlation ($R^2$>0.952) between the water activity value w and the natural logarithmic value of the inactivation rate k. By so doing, it was understood that the inactivation rate k of *B. longum* BAA-999 is proportional to the water activity value w of the composition, and that the relation between the inactivation rate k and the water activity value can be expressed by the following equation (3) which represents the regression line of FIG. 6.

$$Ln\ k = k'w + C \qquad (3)$$

k': slope (regression coefficient) of the linear regression line of FIG. 6 w: water activity value of the composition

C: Y-intercept of the regression line of FIG. 6

Then, the equation (2) was substituted into the equation (3), by which the following equation (4) was derived.

$$Ln\ \{(N_0 - N_t)/t\} = k'w + C \qquad (4)$$

Furthermore, the equation (4) can be modified into the following equation (5) by definition.

$$(N_0 - N_t)/t = EXP(k'w + C) \qquad (5)$$

Furthermore, the equation (5) was converted into the following equation (6).

$$N_t = N_0 - t \times EXP(k'w + C) \qquad (6)$$

In this way, it was revealed that the common logarithmic value ($N_t = Log_{10} n_t$) of the survival cell count $n_t$ (CFU/g) after the storage period t (days) can be expressed by the equation (6).

From these, it was shown that the survival cell count $n_t$ (CFU/g) of the strain *B. longum* BAA-999 contained in a composition after storage was strongly dependent on the storage temperature (° C.) of the composition and the water activity value w of the composition. From this result, it was assumed to be possible to estimate the survival cell count $n_t$ (CFU/g) of the strain contained in a composition after storage, by using the storage temperature (° C.) of the composition and the water activity value w of the composition. Consequently, equations of these regression lines at respective storage temperatures (° C.) were calculated from the regression lines of FIG. 6. The thus obtained equations are shown in Table 6.

TABLE 6

| Storage temperature | Equation of regression line | Correlation coefficient |
|---|---|---|
| 25° C. | y = 12.08x − 6.8239 | $R^2$ = 0.9953 |
| 37° C. | y = 13.269x − 4.362 | $R^2$ = 0.9516 |
| 45° C. | y = 15.118x − 3.06 | $R^2$ = 0.994 |
| 60° C. | y = 18.411x − 0.508 | $R^2$ = 0.9695 |

Here, as the equations of the regression lines at respective storage temperatures (° C.) shown in Table 6 represent the above-mentioned equation (3), the coefficients k' and the constants C at respective storage temperatures (° C.) can be obtained from Table 6. The results thereof were k'=12.02, C=−6.8176 at the storage temperature of 25° C., k'=13.122, C=−4.321 at the storage temperature of 37° C., k'=15.130, C=−3.051 at the storage temperature of 45° C., and k'=18.000, C=−0.459 at the storage temperature of 60° C.

Figure 7:
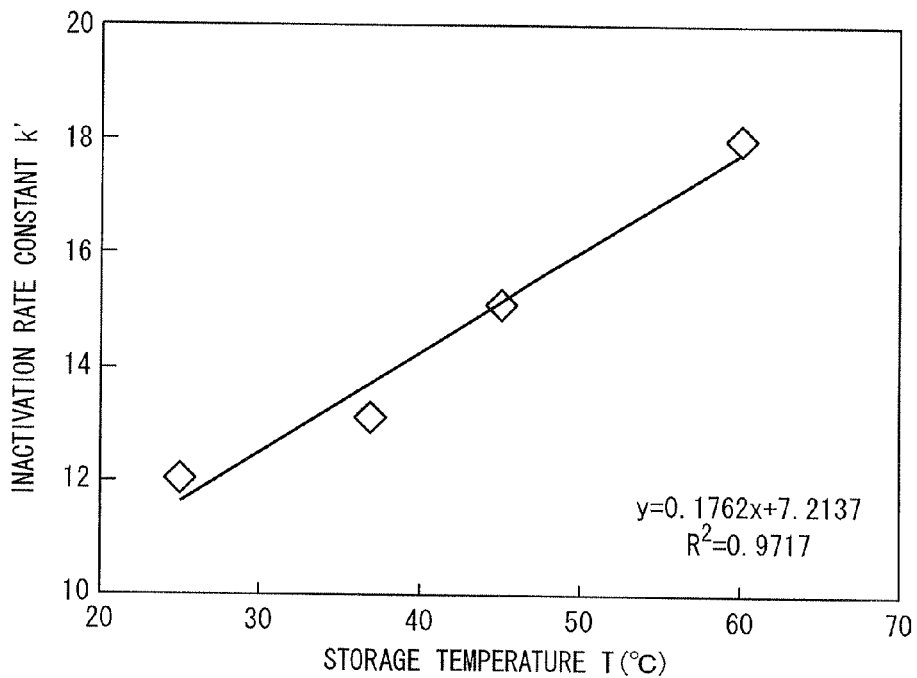
FIG. 7 shows a relation between the inactivation rate constant k' of *B. longum* BAA-999 and the storage temperature (° C.).
Figure 8:
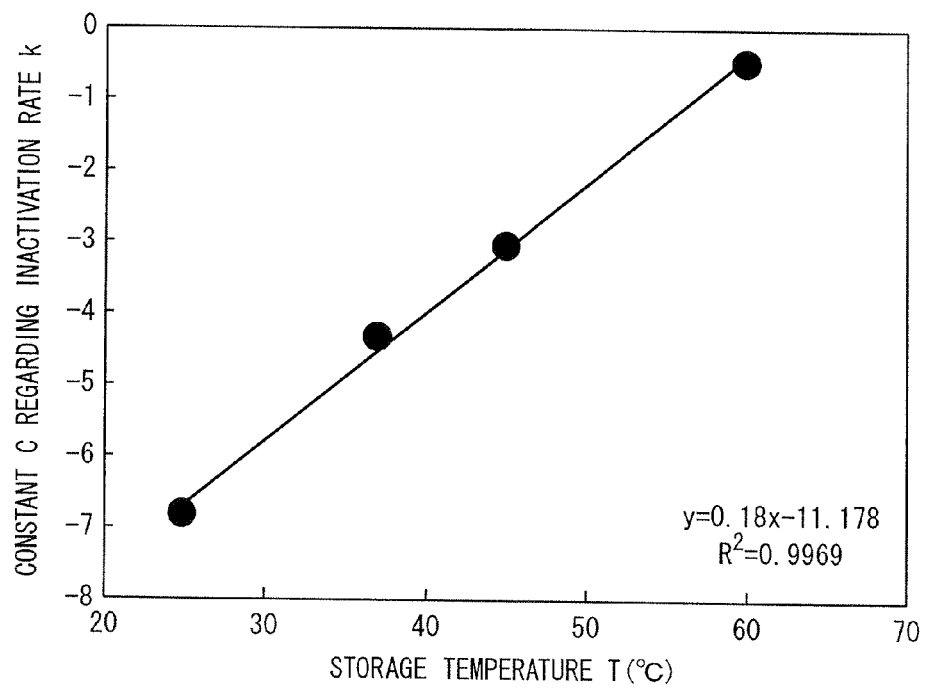
FIG. 8 shows a relation between the constant C regarding the inactivation rate k of *B. longum* BAA-999 and the storage temperature (° C.).

Then, the relation between the coefficient k' at respective storage temperature and the storage temperature (° C.) was plotted, from which the regression line expressed by y=0.1762x+7.2137 was derived as shown in FIG. 7. Moreover, the relation between the constant C at respective storage temperature and the storage temperature (° C.) was plotted, from which the regression line expressed by y=0.18x−11.178 was derived as shown in FIG. 8. In addition, the respective correlation coefficients thereof were shown to be very high at $R^2=0.9717$ and $R^2=0.9969$. From this, it was proven that the coefficient k' and the constant C are able to be expressed by the following equation (7) and the following equation (8).

$$k'=0.1762 \times T+7.2137 \quad (7)$$

$$C=0.18 \times T-11.178 \quad (8)$$

T: storage temperature (° C.)

The equation (7) corresponds to $(k'=A_T \times T+B_T)$ in the above-mentioned equation (I), and the equation (8) corresponds to $(C=C_T \times T+D_T)$ in the above-mentioned equation (I). That is, in this example, $A_T=0.1762$, $B_T=7.2137$, $C_T=0.18$, and $D_T=11.178$.

Then, by substituting the equation (7) and the equation (8) into the equation (6), the following equation (9) was derived.

$$N_t=N_0-t \times \text{EXP}\{(0.1762 \times T+7.2137)w+(0.18 \times T-11.178)\} \quad (9)$$

Furthermore, $N_t$ and $N_0$ were subjected to logarithmic transformation, and the following equation (10) was derived in the end.

$$\text{Log}_{10} n_t = \text{Log}_{10} n_0 - t \times \text{EXP}\{(0.1762 \times T+7.2137)w+(0.18 \times T-11.178)\} \quad (10)$$

From these, it was revealed that *B. longum* BAA-999 contained at a viable cell count $n_0$ (CFU/g) in the composition at the initiation of storage will show a survival cell count $n_t$ (CFU/g) after a storage period t (days) when stored at a storage temperature T (° C.) in a storage condition with a water activity value w, which can be expressed by the above-mentioned equation (10). Moreover, it was shown from the equation (10) that the survival cell count $n_t$ (CFU/g) changes depending on the viable cell count $n_0$ (CFU/g) of the strain contained in the composition at the initiation of storage, the storage temperature T (° C.), the storage period t (days), and the water activity value w.

Accordingly, with the equation (10), it is possible to estimate the survival cell count $n_t$ (CFU/g) of *B. longum* BAA-999 contained in the composition after a storage period t (days), by determining the viable cell count $n_0$ (CFU/g) of the strain at the initiation of storage, the storage temperature T (° C.), the storage period t (days), and the water activity value w.

Test example 2

Test with *Bifidobacterium breve* BCCM LMG 23729

Methods

The test was carried out in the same manner as that of the test example 1, except for that a bacterial powder of *Bifidobacterium breve* BCCM LMG 23729 (*Bifidobacterium breve* M16V, manufactured by Morinaga Milk Industry Co., Ltd; hereunder, abbreviated as *B. breve* LMG 23729) was used as a test bacterium, a storage temperature (° C.) of 5° C. was added, and the water activity value w of raw starch of respective sample was changed as of the following Table 7 by modifying the ratio of raw starch to dry starch.

Results

Similarly to the test example 1, the survival cell count $n_t$ (CFU/g) in the sample was measured. From the regression line regarding its survivability, the inactivation rates k of *B. breve* LMG 23729 in respective storage conditions were calculated, and the results are as shown in Table 7.

TABLE 7

| Storage temperature | Water activity value w | | | | | | |
|---|---|---|---|---|---|---|---|
| | 0.51 | 0.33 | 0.27 | 0.22 | 0.16 | 0.11 | 0.04 |
| 60° C. | N.D. | N.D. | 42.918 | 13.995 | 5.0323 | 2.4053 | 0.4181 |
| 45° C. | N.D. | 7.0597 | 5.6308 | 1.6583 | 1.1505 | 0.4001 | N.D. |
| 37° C. | 3.3085 | 0.5401 | 0.2828 | 0.0762 | 0.0439 | 0.021 | 0.0147 |
| 25° C. | N.D. | 0.0323 | 0.0154 | 0.007 | 0.005 | N.D. | N.D. |
| 5° C. | N.D. | 0.0319 | N.D. | N.D. | N.D. | N.D. | N.D. |

Figure 9:
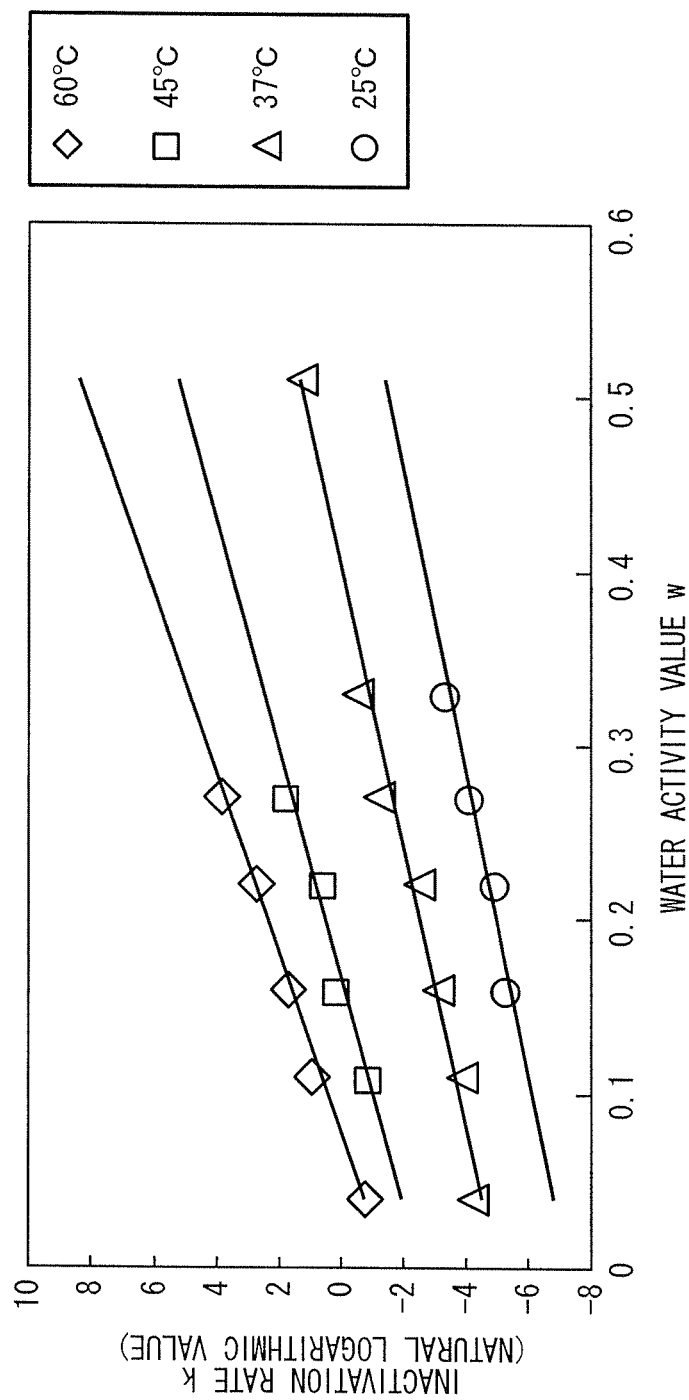
FIG. 9 shows relations between the water activity value w and the inactivation rate k of *B. breve* LMG 23729 at respective storage temperatures (° C.).

In addition, the relation between the natural logarithmic value of the inactivation rate k and the water activity value w of Table 7 was plotted. As a result, it was shown that, at any storage temperature (° C.), there was a strong positive correlation ($R^2>0.9499$) between the inactivation rate k and the water activity value w, as shown in FIG. 9. Accordingly, the inactivation rate k of *B. breve* LMG 23729 was shown to be proportional to the water activity value w of the composition, similarly to the test example 1.

Then, it was revealed that, similarly to the test example 1, the following equation (11) can work out with *B. breve* LMG 23729, similar to the above-mentioned equation (6) of the test example 1, by using the storage period t (days), the storage temperature T (° C.), and the water activity value w, provided that the symbol $n_t$ stands for the survival cell count (CFU/g) after storage and the symbol $n_0$ stands for the bacterial count (CFU/g) at the initiation of storage.

$$N_t=N_0-t \times \text{EXP}(k'w+C) \quad (11)$$

From these, it was shown that the survival cell count $n_t$ (CFU/g) of the strain *B. breve* LMG 23729 contained in a composition after storage was strongly dependent on the storage temperature T (° C.) of the composition and the water activity value w of the composition, similarly to the test example 1. From this result, it was assumed to be possible to estimate the survival cell count $n_t$ (CFU/g) of the strain contained in a composition after storage, by using the storage temperature T (° C.) of the composition and the water activity value w of the composition. Consequently, equations of these regression lines at respective storage temperatures (° C.) were calculated from the regression lines of FIG. 10. The thus obtained equations are shown in Table 8.

TABLE 8

| Storage temperature | Equation of regression line | Correlation coefficient |
|---|---|---|
| 25° C. | y = 11.346x − 7.247 | $R^2 = 0.9679$ |
| 37° C. | y = 12.346x − 4.9591 | $R^2 = 0.9787$ |
| 45° C. | y = 15.242x − 2.5315 | $R^2 = 0.9499$ |
| 60° C. | y = 19.405x − 1.5009 | $R^2 = 0.992$ |

Here, similarly to the test example 1, the coefficients k' and the constants C at respective storage temperatures (° C.) can be obtained from Table 8. The results thereof were k'=11.346, C=−7.247 at the storage temperature of 25° C., k'=12.346, C=−4.9591 at the storage temperature of 37° C., k'=15.242, C=−2.5315 at the storage temperature of 45° C., and k'=19.405, C=−1.5009 at the storage temperature of 60° C.

Then, the relation between the coefficient k' at respective storage temperature and the temperature (° C.) was plotted to obtain the regression line, from which y=0.2396x+4.5794 was derived. Moreover, the relation between the constant C at respective temperature and the storage temperature (° C.) was plotted to obtain the regression line, from which y=0.691x−11.118 was derived. In addition, the correlation coefficients of the respective equations were $R^2$=0.9483 and $R^2$=0.931, showing a strong correlation between the constant C at respective temperature and the storage temperature (° C.) similarly to the test example 1. From this, it was proven that the coefficient k' and the constant C of *B. breve* LMG 23729 are able to be expressed by the following equation (12) and the following equation (13).

$$k'=0.2396 \times T+4.5794 \quad (12)$$

$$C=0.691 \times T-11.118 \quad (13)$$

The equation (12) corresponds to (k'=$A_T \times T+B_T$) in the above-mentioned equation (I), and the equation (13) corresponds to (C=$C_T \times T+D_T$) in the above-mentioned equation (I). That is, in this example, $A_T$=0.2396, $B_T$=4.5794, $C_T$=0.691, and $D_T$=−11.118.

T: storage temperature (° C.)

Then, by substituting the equation (12) and the equation (13) into the equation (11), and further by logarithmically transforming $N_0$ into $Log_{10} n_0$ and $N_t$ into $Log_{10} n_t$, the following equation (14) was derived.

$$Log_{10} n_t=Log_{10} n_0-t \times EXP\{(0.2396 \times T+4.5794)w+ (0.691 \times T-11.118)\} \quad (14)$$

With the equation (14), it is possible to estimate the survival cell count $n_t$ (CFU/g) of *B. breve* LMG 23729 contained in the composition after a storage period t (days), by determining the viable cell count $n_0$ (CFU/g) of the strain at the initiation of storage, the storage temperature T (° C.), the storage period t (days), and the water activity value w.

Test example 3

Test with *Bifidobacterium pseudolongum* IFO 15861

Methods

The test was carried out in the same manner as that of the test example 1, except for that a bacterial powder of *Bifidobacterium pseudolongum* IFO 15861 (*Bifidobacterium pseudolongum* M-602, manufactured by Morinaga Milk Industry Co., Ltd; hereunder, abbreviated as *B. pseudolongum* IFO 15861) was used as a test bacterium, and the water activity value w of raw starch of respective sample was changed as of the following Table 9 by modifying the ratio of raw starch to dry starch.

Results

Similarly to the test example 1, the survival cell count $n_t$ (CFU/g) in the sample was measured. From the regression line regarding its survivability, the inactivation rates k of *B. pseudolongum* IFO 15861 in respective storage conditions were calculated and the results are as shown in Table 9.

TABLE 9

| Storage temperature | Water activity value w | | | | | | |
|---|---|---|---|---|---|---|---|
| | 0.53 | 0.34 | 0.28 | 0.23 | 0.18 | 0.12 | 0.06 |
| 60° C. | N.D. | N.D. | 26.757 | 12.438 | 2.8028 | 2.1649 | 0.5457 |
| 45° C. | N.D. | 5.9646 | 1.7352 | 0.9849 | 0.4273 | 0.1283 | 0.0708 |
| 37° C. | N.D. | 0.3008 | 0.1942 | 0.0727 | 0.0522 | 0.0189 | −0.004 |
| 25° C. | 0.9498 | 0.0234 | N.D. | N.D. | N.D. | 0.0061 | N.D. |

Figure 10:
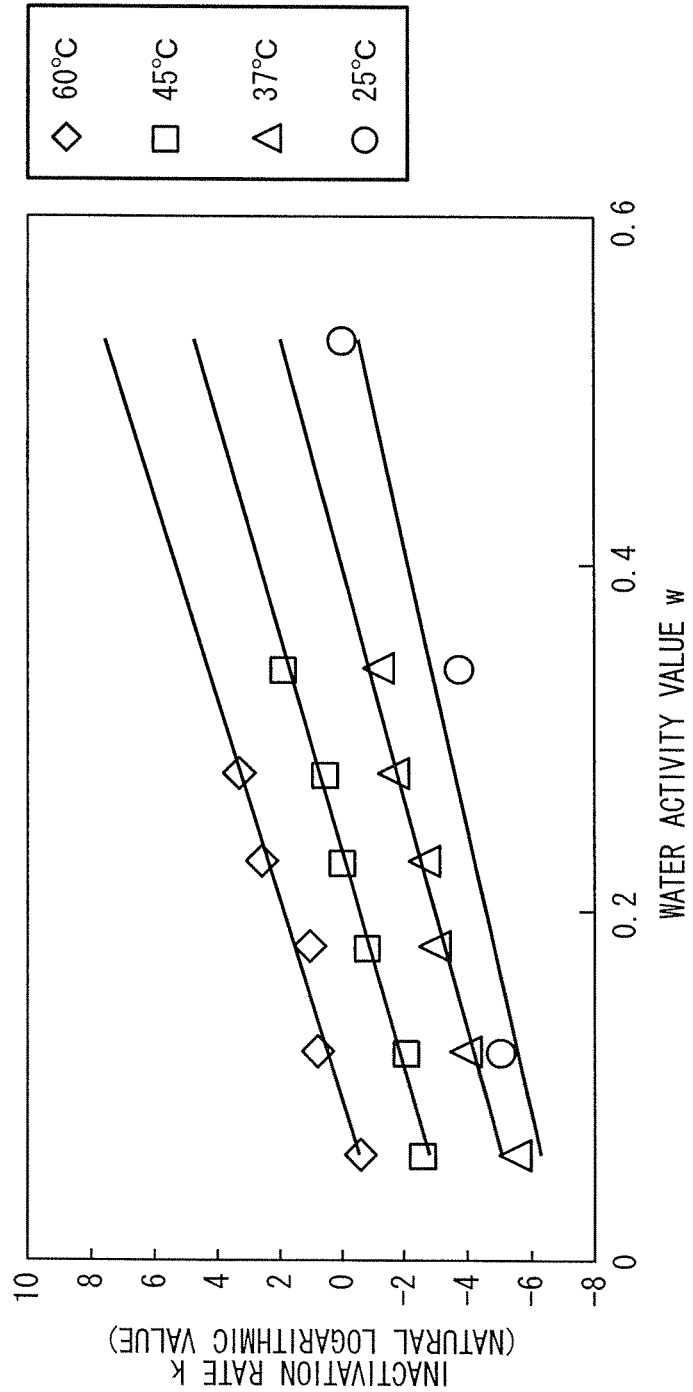
FIG. 10 shows relations between the water activity value w and the inactivation rate k of *B. pseudolongum* IFO 15861 at respective storage temperatures (° C.).

In addition, the relation between the natural logarithmic value of the inactivation rate k and the water activity value w of Table 9 was plotted. As a result, it was shown that, at any storage temperature (° C.), there was a strong positive correlation ($R^2$>0.91) between the inactivation rate k and the water activity value w, as shown in FIG. 10. Accordingly, the inactivation rate k of *B. pseudolongum* IFO 15861 was shown to be proportional to the water activity value w of the composition, similarly to the test example 1.

Then, it was revealed that, similarly to the test example 1, the following equation (15) can work out with *B. pseudolongum* IFO 15861, like the above-mentioned equation (6) of the test example 1, by using the storage period t (days), the storage temperature T (° C.), and the water activity value w, provided that the symbol $n_t$ stands for the survival cell count (CFU/g) after storage and the symbol $n_0$ stands for the bacterial count (CFU/g) at the initiation of storage.

$$N_t=N_0-t \times EXP(k'w+C) \quad (15)$$

From these, it was shown that the survival cell count $n_t$ (CFU/g) of the strain *B. pseudolongum* IFO 15861 contained in a composition after storage was strongly dependent on the storage temperature T (° C.) of the composition and the water activity value w of the composition, similarly to the test example 1. From this result, it was assumed to be possible to estimate the survival cell count $n_t$ (CFU/g) of the strain contained in a composition after storage, by using the storage temperature T (° C.) of the composition and the water activity value w of the composition. Consequently, equations of these regression lines at respective storage temperatures (° C.) were calculated from the regression lines of FIG. 12. The thus obtained equations are shown in Table 10.

TABLE 10

| Storage temperature | Equation of regression line | Correlation coefficient |
|---|---|---|
| 25° C. | y = 12.192x − 6.9977 | $R^2$ = 0.9108 |
| 37° C. | y = 15.039x − 6.0165 | $R^2$ = 0.9622 |
| 45° C. | y = 15.973x − 3.7595 | $R^2$ = 0.9918 |
| 60° C. | y = 17.252x − 1.601 | $R^2$ = 0.9632 |

The coefficients k' and the constants C at respective storage temperatures (° C.) can be obtained from Table 10. The results thereof were k'=11.346, C=−7.247 at the storage temperature of 25° C., k'=12.346, C=−4.9591 at the storage temperature of 37° C., k'=15.242, C=−2.5315 at the storage temperature of 45° C., and k'=19.405, C=−1.5009 at the storage temperature of 60° C.

Then, the relation between the coefficient k' at respective temperature and the temperature (° C.) was plotted to obtain the regression line, from which y=0.1409x+9.2317 was derived. Moreover, the relation between the constant C at respective temperature and the storage temperature (° C.) was plotted to obtain the regression line, from which y=0.1614x−11.33 was derived. In addition, the correlation coefficients of the respective equations were $R^2$=0.9266 and $R^2$=0.9646, showing similar correlation to that of the test example 1. From this, it was proven that the coefficient k' and the constant C of *B. pseudolongum* IFO 15861 are able to be expressed by the following equation (16) and the following equation (17).

$$k'=0.1409 \times T + 9.2317 \quad (16)$$

$$C=0.1614 \times T - 11.33 \quad (17)$$

The equation (16) corresponds to $(k'=A_T \times T + B_T)$ in the above-mentioned equation (I), and the equation (17) corresponds to $(C=C_T \times T + D_T)$ in the above-mentioned equation (I). That is, in this example, $A_T$=0.1409, $B_T$=9.2317, $C_T$=0.1614, $D_T$=−11.33.

T: storage temperature (° C.)

Then, by substituting the equation (16) and the equation (17) into the equation (15), and further by logarithmically transforming $N_0$ into $Log_{10} n_0$ and $N_t$ into $Log_{10} n_t$, the following equation (18) was derived.

$$Log_{10} n_t = Log_{10} n_0 - t \times EXP\{(0.1409 \times T + 9.2317)w + (0.1614 \times T - 11.33)\} \quad (18)$$

With the equation (18), it is possible to estimate the survival cell count $n_t$ (CFU/g) of *B. pseudolongum* IFO 15861 contained in the composition after a storage period t (days), by determining the viable cell count $n_0$ (CFU/g) of the strain at the initiation of storage, the storage temperature T (° C.), the storage period t (days), and the water activity value w.

Hereunder is another description of the method for deriving the above-mentioned equation (I) used in the method for estimating survival cell count and the method for setting a guaranteed cell count of lactic acid bacteria, with reference to the test example 4.

Test example 4

Test with *Lactobacillus acidophilus* LAC-300

Methods

The test was carried out in the same manner as that of the test example 1, except for that a bacterial powder of *Lactobacillus acidophilus* IFO-15862 (*Lactobacillus acidophilus* LAC-300, manufactured by Morinaga Milk Industry Co., Ltd; hereunder, abbreviated as *L. acidophilus* LAC-300) was used as a test bacterium, the storage temperature (° C.) was set at 30° C. rather than 25° C., the water activity value w of raw starch of respective sample was changed as of the following Table 11 by modifying the ratio of raw starch to dry starch, and the culture was performed under an aerobic condition rather than the anaerobic condition for the measurement of the survival cell count $n_t$ (CFU/g).

Results

Similarly to the test example 1, the survival cell count $n_t$ (CFU/g) in the sample was measured. From the regression line regarding its survivability, the inactivation rates k of *L. acidophilus* LAC-300 in respective storage conditions were calculated and the results are as shown in Table 11.

TABLE 11

| Storage temperature | Water activity value w | | | | |
|---|---|---|---|---|---|
| | 0.55 | 0.3 | 0.23 | 0.15 | 0.01 |
| 60° C. | N.D. | N.D. | 43.37 | 9.112 | 0.895 |
| 45° C. | N.D. | 6.7053 | 0.7342 | 0.4736 | N.D. |
| 37° C. | 20.128 | 1.0547 | 0.1321 | 0.073 | N.D. |
| 30° C. | 5.9242 | 0.0888 | N.D. | 0.0481 | N.D. |

Figure 13:
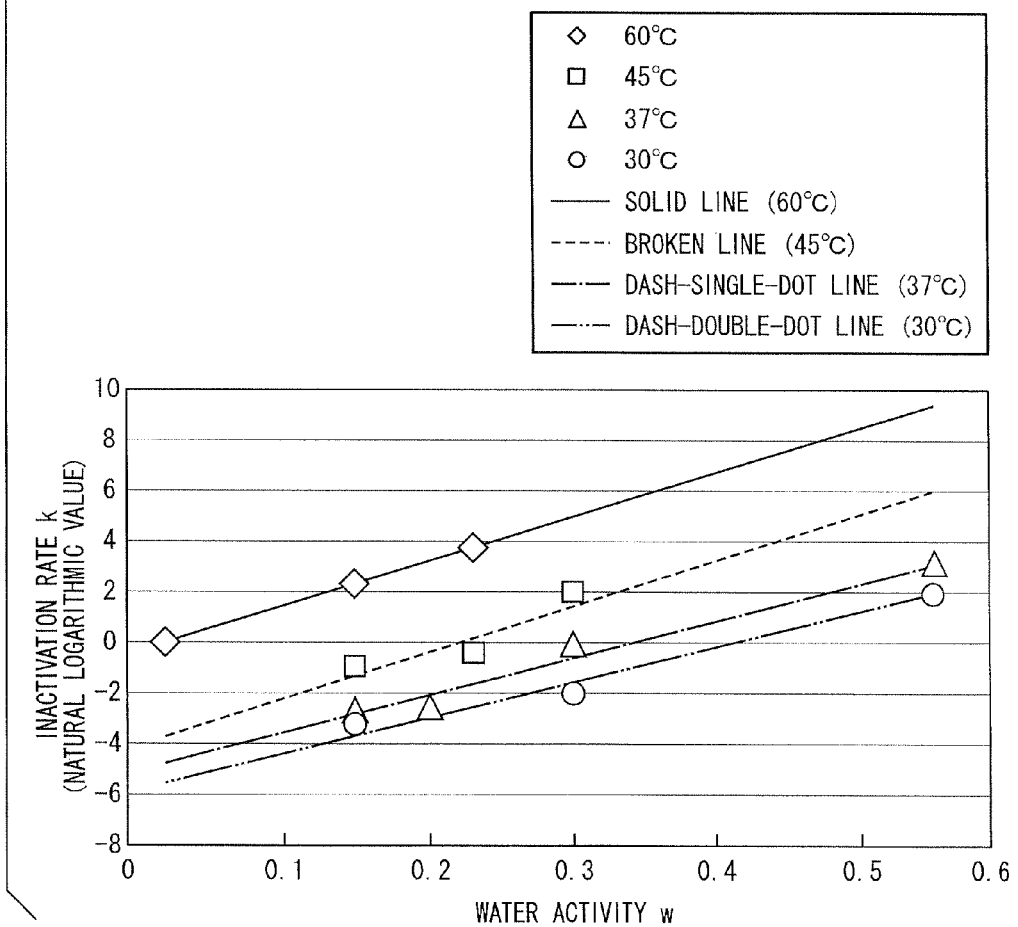
FIG. 13 shows relations between the water activity value w and the inactivation rate k (natural logarithmic value) of *L. acidophilus* LAC-300.

In addition, the relation between the natural logarithmic value of the inactivation rate k and the water activity value w of Table 11 was plotted. As a result, it was shown that, at any storage temperature (° C.), there was a strong positive correlation ($R^2$>0.8876) between the inactivation rate k and the water activity value w, as shown in FIG. 13. Accordingly, the inactivation rate k of *L. acidophilus* LAC-300 was shown to be proportional to the water activity value w of the composition, similarly to the test example 1.

Then, it was revealed that, similarly to the test example 1, the following equation (19) can work out with *L. acidophilus* LAC-300, like the above-mentioned equation (6) of the test example 1, by using the storage period t (days), the storage temperature T (° C.), and the water activity value w, provided that the symbol $n_t$ stands for the survival cell count (CFU/g) after storage and the symbol $n_0$ stands for the bacterial count (CFU/g) at the initiation of storage.

$$N_t = N_0 - t \times EXP(k'w + C) \quad (19)$$

From these, it was shown that the survival cell count $n_t$ (CFU/g) of the strain *L. acidophilus* LAC-300 contained in a composition after storage was strongly dependent on the storage temperature T (° C.) of the composition and the water activity value w of the composition, similarly to the test example 1. From this result, it was assumed to be possible to estimate the survival cell count $n_t$ (CFU/g) of the strain contained in a composition after storage, by using the storage temperature T (° C.) of the composition and the water activity value w of the composition. Consequently, equations of these regression lines at respective storage temperatures (° C.) were calculated from the regression lines of FIG. 13. The thus obtained equations are shown in Table 12.

TABLE 12

| Storage temperature | Equation of regression line | Correlation coefficient |
|---|---|---|
| 30° C. | y = 13.135x − 5.7123 | $R^2$ = 0.9484 |
| 37° C. | y = 14.526x − 4.8705 | $R^2$ = 0.9767 |
| 45° C. | y = 17.72x − 3.7463 | $R^2$ = 0.8876 |
| 60° C. | y = 17.976x − 0.3807 | $R^2$ = 0.9948 |

Here, similarly to the test example 1, the coefficients k' and the constants C at respective storage temperatures (° C.) can be obtained from Table 12. The results thereof were k'=13.135, C=−5.7123 at the storage temperature of 30° C., k'=14.526, C=−4.8705 at the storage temperature of 37° C., k'=17.72, C=−3.7463 at the storage temperature of 45° C., and k'=13.135, C=−5.7123 at the storage temperature of 60° C.

Then, the relation between the coefficient k' at respective temperature and the temperature (° C.) was plotted to obtain the regression line, from which y=0.1669x+8.6621 was derived. Moreover, the relation between the constant C at respective temperature and the storage temperature (° C.) was plotted to obtain the regression line, from which y=0.1839x−11.327 was derived. In addition, the correlation coefficients of the respective equations were $R^2=0.86621$ and $R^2=0.9853$, showing similar correlation to that of the test example 1. From this, it was proven that the coefficient k' and the constant C of *L. acidophilus* LAC-300 are able to be expressed by the following equation (20) and the following equation (21).

$$k'=0.1669 \times T+8.6621 \quad (20)$$

$$C=0.1839 \times T-11.327 \quad (21)$$

The equation (20) corresponds to ($k'=A_T \times T+B_T$) in the above-mentioned equation (I), and the equation (21) corresponds to ($C=C_T \times T+D_T$) in the above-mentioned equation (I). That is, in this example, $A_T=0.1669$, $B_T=8.6621$, $C_T=0.1839$, and $D_T=-11.327$.

T: storage temperature (° C.)

Then, by substituting the equation (20) and the equation (21) into the equation (19), and further by logarithmically transforming $N_0$ into $Log_{10} n_0$ and $N_t$ into $Log_{10} n_t$, the following equation (22) was derived.

$$Log_{10} n_t = Log_{10} n_0 - t \times EXP\{(0.1669 \times T+8.6621)w+ (0.1839 \times T-11.327)\} \quad (22)$$

With the equation (22), it is possible to estimate the survival cell count $n_t$ (CFU/g) of *L. acidophilus* LAC-300 contained in the composition after a storage period t (days), by determining the viable cell count $n_0$ (CFU/g) of the strain at the initiation of storage, the storage temperature T (° C.), the storage period t (days), and the water activity value w.

In the test example 1 through the test example 3, all the strains were bacterial belonging to the genus *Bifidobacterium*. However, because the Non-patent Document 8 showed that the survivability of lactic acid bacteria is also dependent on the storage temperature and the water activity value, the method for estimating survival cell count of the present invention is applicable to this bacteria, the detail of which is shown in the test example 4. Furthermore, the survival cell count estimation method of the present invention is also applicable to another strain belonging to a different bacterial genus, in the same manner as that of the test example 1 through the test example 4, as long as the survivability of the strain is proven to be dependent on the storage temperature and the water activity value.

A method for estimating a survival cell count of the present invention is able to calculate an accurately estimated result of the survival cell count of a specific strain in a probiotic product with respect to its storage period and to shorten the time for developing the product.

A method for setting a guaranteed cell count of the present invention is able to readily calculate a guaranteed cell count of a specific strain in a probiotic product within its quality guarantee period.

Next, the structure and the process of the device for estimating survival cell count with use of the method for estimating survival cell count of the above is explained below.

Figure 11:
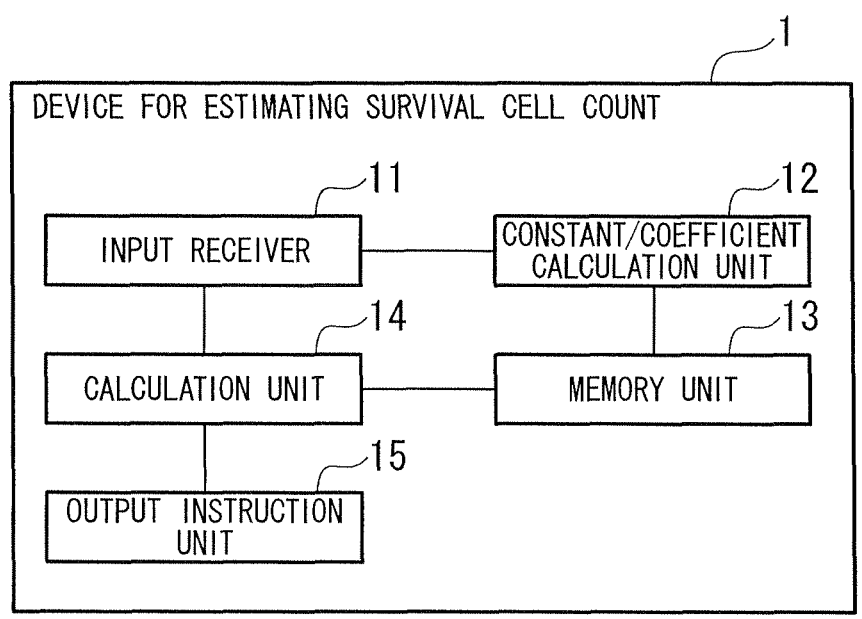
FIG. 11 is a block diagram showing the structure of a device for estimating survival cell count.

FIG. 11 is a block diagram showing the structure of a device 1 for estimating survival cell count according to one embodiment of the present invention. The device 1 for estimating survival cell count can be realized by a computer device such as a personal computer, and comprises an input receiver 11, a constant/coefficient calculation unit 12, a memory unit 13, a calculation unit 14, and an output instruction unit 15.

The input receiver 11 receives an input of information entered by the user through an input unit such as a keyboard, a mouse, a touch panel, a button, and a key. Alternatively, the input receiver 11 may also receive information from another computer device linked through a network, or may read out information from a computer-readable recording medium.

The constant/coefficient calculation unit 12 calculates $A_T$, $B_T$, $C_T$, and $D_T$ serving as the coefficients and the constants for use in the equation (I), and writes them into the memory unit 13. In accordance with the equation (I) using $A_T$, $B_T$, $C_T$, and $D_T$ stored in the memory unit 13, the calculation unit 14 calculates a survival cell count of a strain contained in a composition after a storage period, a storage period of a composition containing a strain, a viable cell count of a strain contained in a composition at the initiation of storage, a storage temperature of a composition, or a water activity value of a composition. Moreover, the calculation unit 14 calculates a guaranteed cell count in accordance with the equation (II).

The output instruction unit 15 has a function to output the calculation result from the calculation unit 14 to an output unit, for example, to display the result on CRT (cathode ray tube), LCD (liquid crystal display), or such a display panel, or to print out the result using a printer or the like. Alternatively, the output instruction unit 15 may also write the calculation result from the calculation unit 14 into a computer-readable recording medium, or may output the result to another computer device linked through a network.

Next is a description of the process for calculating $A_T$, $B_T$, $C_T$, and $D_T$ serving as the coefficients and the constants of the equation (I), by using the device 1 for estimating survival cell count.

First, the input receiver 11 of the device 1 for estimating survival cell count receives an input of information on the type of the strain, the storage condition under which the above-mentioned experiment has been done on the strain, the thus yielded experimental results of the storage temperature (° C.) and the water activity value w of the composition containing the strain, the storage period of the composition (days), and the viable cell count $n_0$ (CFU/g) in the composition after the storage period.

The constant/coefficient calculation unit 12 respectively calculates the first regression line (refer to FIG. 1 to FIG. 4 and Table 5) per each storage condition, that is, per each storage temperature (° C.) and water activity value, by having the common logarithmic value of the survival cell count $n_t$ (CFU/g) of the specific strain in respective sample on the Y-axis and the storage period t (days)×1/30 on the X-axis. The constant/coefficient calculation unit 12 gains the absolute value of the slope (regression coefficient) of the first regression line that has been obtained per each storage condition, as the inactivation rate k of each storage condition.

Next, the constant/coefficient calculation unit 12 respectively calculates the second regression line y=ax+b (refer to FIG. 6 and Table 6) per each storage temperature (° C.), by having the natural logarithmic value of the inactivation rate k at respective storage temperature (° C.) on the Y-axis and the water activity value w on the X-axis.

Furthermore, the constant/coefficient calculation unit 12 calculates the third regression linear equation (refer to FIG. 7) by having the slope (a) of the second regression line on the Y-axis and the storage temperature T (° C.) on the X-axis, to thereby obtain the slope $A_T$ and the Y-intercept $B_T$ of this third regression line.

Subsequently, the constant/coefficient calculation unit 12 calculates the fourth regression linear equation (refer to FIG. 8) by having the constant (b) of the second regression line on the Y-axis and the storage temperature T (° C.) on the X-axis, to thereby obtain the slope $C_T$ and the Y-intercept $D_T$ of this fourth regression line.

The constant/coefficient calculation unit 12 associates the thus calculated $A_T$, $B_T$, $C_T$, and $D_T$ with the information on the type of the bacterium strain and writes the associated data into the memory unit 13.

Next is a description of the process for calculating a survival cell count of a strain contained in a composition after a storage period, a storage period of a composition containing a strain, a viable cell count of a strain contained in a composition at the initiation of storage, a storage temperature of a composition, a water activity value of a composition, and a guaranteed cell count, by using the device 1 for estimating survival cell count.

Calculation of Survival Cell Count of Strain Contained in Composition after Storage Period and Calculation of Guaranteed Cell Count The input receiver 11 of the device 1 for estimating survival cell count receives an input of information on conditions for calculating the survival cell count, that is, the type of the strain, the storage period (days) of the composition containing the strain, the viable cell count $n_0$ (CFU/g) of the strain contained in the composition at the initiation of storage, the storage temperature (° C.) of the composition, and the water activity value w of the composition.

The calculation unit 14 reads out the $A_T$, $B_T$, $C_T$, and $D_T$ corresponding to the input information on the type of the strain from the memory unit 13, and substitutes the storage period (days) of the composition containing the strain, the viable cell count $n_0$ (CFU/g) of the strain contained in the composition at the initiation of storage, the storage temperature (° C.) of the composition, and the water activity value w of the composition, presented by the input information on conditions for calculating the survival cell count, into the equation (I) using the read-out $A_T$, $B_T$, $C_T$, and $D_T$, to thereby calculate the survival cell count $n_t$ (CFU/g) of the bacterium strain contained in the composition after the storage period t (days).

Furthermore, using the calculated survival cell count $n_t$ (CFU/g) of the strain contained in the composition after the storage period t (days), the calculation unit 14 calculates a guaranteed cell count N(CFU/g) when stored at or under a temperature T' (° C.) within a guarantee period t' (days), in accordance with the equation (II). The temperature T' (° C.) and the guarantee period t' (days) are the storage temperature (° C.) of the composition and the storage period (days) of the composition containing the strain, presented by the information on conditions for calculating the survival cell count.

The output instruction unit 15 outputs the information on the survival cell count $n_t$ (CFU/g) of the bacterium strain contained in the composition after the storage period and the guaranteed cell count N(CFU/g) that have been calculated by the calculation unit 14.

Calculation of Storage Period of Composition

The input receiver 11 of the device 1 for estimating survival cell count receives an input of information on conditions for calculating the storage period, that is, the type of the strain, the survival cell count $n_t$ (CFU/g) of the strain contained in the composition after the storage period, the storage temperature (° C.) of the composition containing the strain, the viable cell count $n_0$ (CFU/g) of the strain contained in the composition at the initiation of storage, and the water activity value w of the composition.

The calculation unit 14 reads out the $A_T$, $B_T$, $C_T$, and $D_T$ corresponding to the input information on the type of the strain from the memory unit 13, and substitutes the survival cell count $n_t$ (CFU/g) of the strain contained in the composition after the storage period, the storage temperature (° C.) of the composition, the viable cell count $n_0$ (CFU/g) of the strain contained in the composition at the initiation of storage, and the water activity value w of the composition, presented by the input information on conditions for calculating the storage period, into the equation (I) using the read-out $A_T$, $B_T$, $C_T$, and $D_T$, to thereby calculate the storage period (days) of the composition containing the strain.

The output instruction unit 15 outputs the information on the storage period (days) of the composition containing the strain that has been calculated by the calculation unit 14.

Calculation of Viable Cell Count of Strain Contained in Composition at the Initiation of Storage The input receiver 11 of the device 1 for estimating survival cell count receives an input of information on conditions for calculating the viable cell count at the initiation of storage, that is, the type of the strain, the survival cell count $n_t$ (CFU/g) of the strain contained in the composition after the storage period, the storage period (days) of the composition containing the strain, the storage temperature (° C.) of the composition, and the water activity value w of the composition.

The calculation unit 14 reads out the $A_T$, $B_T$, $C_T$, and $D_T$ corresponding to the input information on the type of the strain from the memory unit 13, and substitutes the survival cell count $n_t$ (CFU/g) of the strain contained in the composition after the storage period, the storage period (days) of the composition containing the strain, the storage temperature (° C.) of the composition, and the water activity value w of the composition, presented by the input information on conditions for calculating the viable cell count at the initiation of storage, into the equation (I) using the read-out $A_T$, $B_T$, $C_T$, and $D_T$, to thereby calculate the viable cell count $n_0$ (CFU/g) of the strain contained in the composition at the initiation of storage.

The output instruction unit 15 outputs the information on the viable cell count $n_0$ (CFU/g) of the strain contained in the composition at the initiation of storage that has been calculated by the calculation unit 14.

Calculation of Storage Temperature of Composition

The input receiver 11 of the device 1 for estimating survival cell count receives an input of information on conditions for calculating the storage temperature, that is, the type of the strain, the survival cell count $n_t$ (CFU/g) of the strain contained in the composition after the storage period, the viable cell count $n_0$ (CFU/g) of the strain contained in the composition at the initiation of storage, the storage period (days) of the composition containing the strain, and the water activity value w of the composition.

The calculation unit 14 reads out the $A_T$, $B_T$, $C_T$, and $D_T$ corresponding to the input information on the type of the strain from the memory unit 13, and substitutes the survival cell count $n_t$ (CFU/g) of the strain contained in the composition after the storage period, the viable cell count $n_0$ (CFU/g) of the strain contained in the composition at the initiation of storage, the storage period (days) of the composition containing the strain, and the water activity value w of the composition, presented by the input information on conditions for calculating the storage temperature, into the equation (I) using the read-out $A_T$, $B_T$, $C_T$, and $D_T$, to thereby calculate the storage temperature (° C.) of the composition.

The output instruction unit 15 outputs the information on the storage temperature (° C.) of the composition that has been calculated by the calculation unit 14.

Calculation of Water Activity Value of Composition

The input receiver 11 of the device 1 for estimating survival cell count receives an input of information on conditions for calculating the water activity value, that is, the type of the strain, the survival cell count $n_t$ (CFU/g) of the strain contained in the composition after the storage period, the viable cell count $n_0$ (CFU/g) of the strain contained in the composition at the initiation of storage, the storage period (days) of the composition containing the strain, and the storage temperature (° C.) of the composition.

The calculation unit 14 reads out the $A_T$, $B_T$, $C_T$, and $D_T$ corresponding to the input information on the type of the strain from the memory unit 13, and substitutes the survival cell count $n_t$ (CFU/g) of the strain contained in the composition after the storage period, the viable cell count $n_0$ (CFU/g) of the strain contained in the composition at the initiation of storage, the storage period (days) of the composition containing the strain, and the storage temperature (° C.) of the composition, presented by the input information on conditions for calculating the water activity value, into the equation (I) using the read-out $A_T$, $B_T$, $C_T$, and $D_T$, to thereby calculate the water activity value w of the composition.

The output instruction unit 15 outputs the information on the water activity value w of the composition that has been calculated by the calculation unit 14.

In the above-mentioned process, if the standard unit of the input information of each condition is different from the standard unit for use in the equation (I), the unit of the input information of each condition has to be converted into the unit for use in the equation (I) before substitution.

Figure 12:
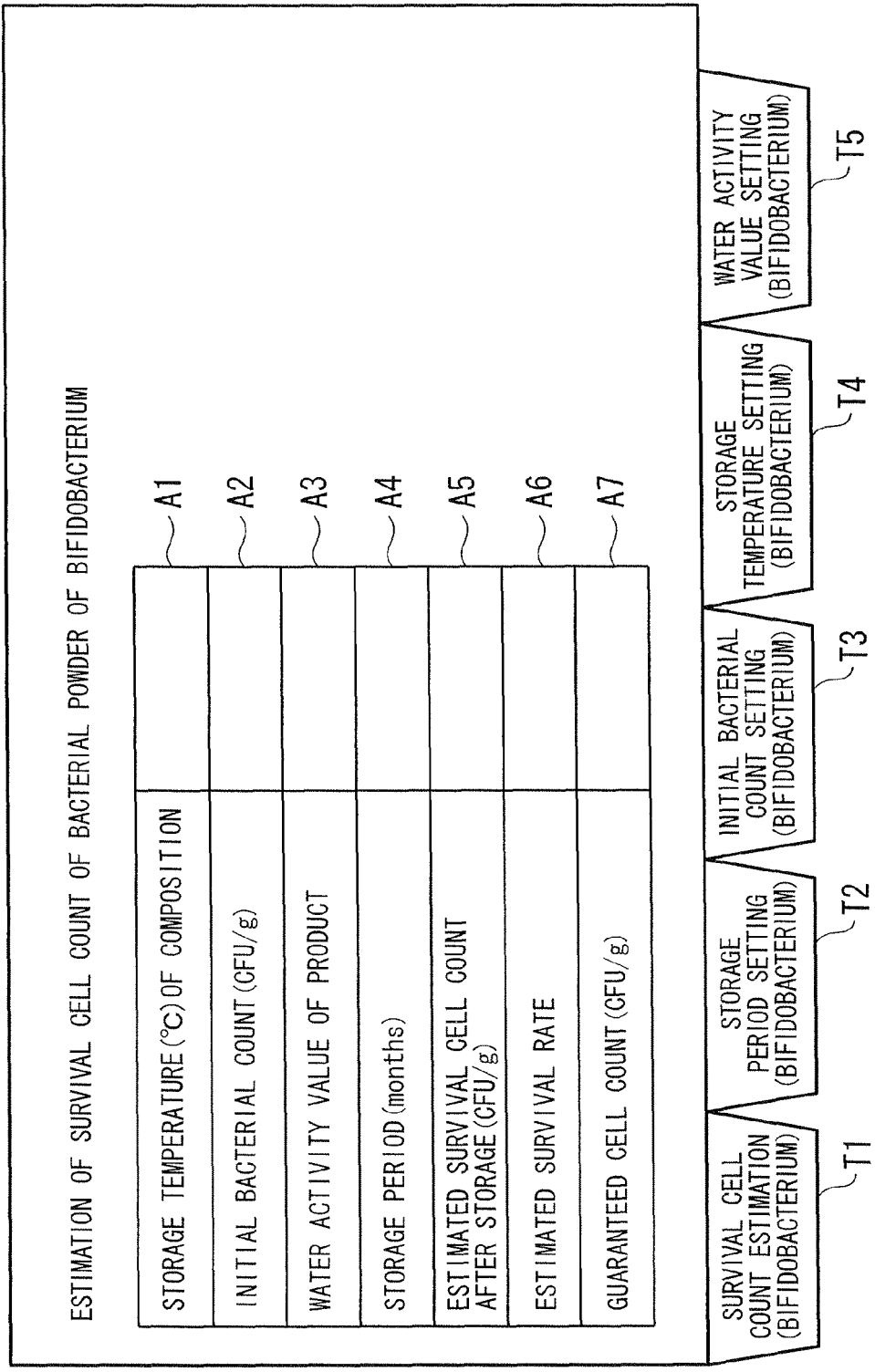
FIG. 12 shows an example of a display screen image output from the device for estimating survival cell count.

FIG. 12 shows an example of an image output from the device 1 for estimating survival cell count.

In this image, firstly, a tab corresponding to the strain type and the calculation object are selected from the tabs T1 to T5 by the input unit of the device 1 for estimating survival cell count. This image shows the case where *bifidobacterium* is selected as the strain type and the survival cell count of the strain contained in a composition after a storage period (survival cell count estimation) is selected as the calculation object, by the tab T1.

This image also shows a field an input field A1 for entering a storage temperature (° C.) of the composition, an input field A2 for entering a viable cell count $n_0$ (CFU/g) of the strain contained in the composition at the initiation of storage (initial bacterial count), an input field A3 for entering a water activity value of the composition, and an input field A4 for entering a storage period (months) of the composition containing the strain. When the user enters these numerical values into the input fields A1 to A4 by the input unit of the device 1 for estimating survival cell count, the calculation unit 14 of the device 1 for estimating survival cell count calculates the survival cell count $n_t$ (CFU/g) of the bacterium strain contained in the composition after the storage period, by substituting the values that have been entered into the input fields A1 to A4, into the equation (I) using the $A_T$, $B_T$, $C_T$, and $D_T$ corresponding to the selected strain type, in this case, *bifidobacterium*, and the output instruction unit 15 displays the calculation result in the display field A5. The equation (I) using the $A_T$, $B_T$, $C_T$, and $D_T$ corresponding to *bifidobacterium* can be exemplified by the equation (10) in the test example 1.

In this image, the output instruction unit 15 further displays the estimated survival rate (survival cell count of the bacterium strain contained in the composition after the storage period)/(viable cell count of the strain contained in the composition at the initiation of storage) calculated by the calculation unit 14, in the display field A6, and displays the guaranteed cell count N(CFU/g) calculated by the calculation unit 14 in accordance with the equation (II), in the display field A7.

Figure 14:
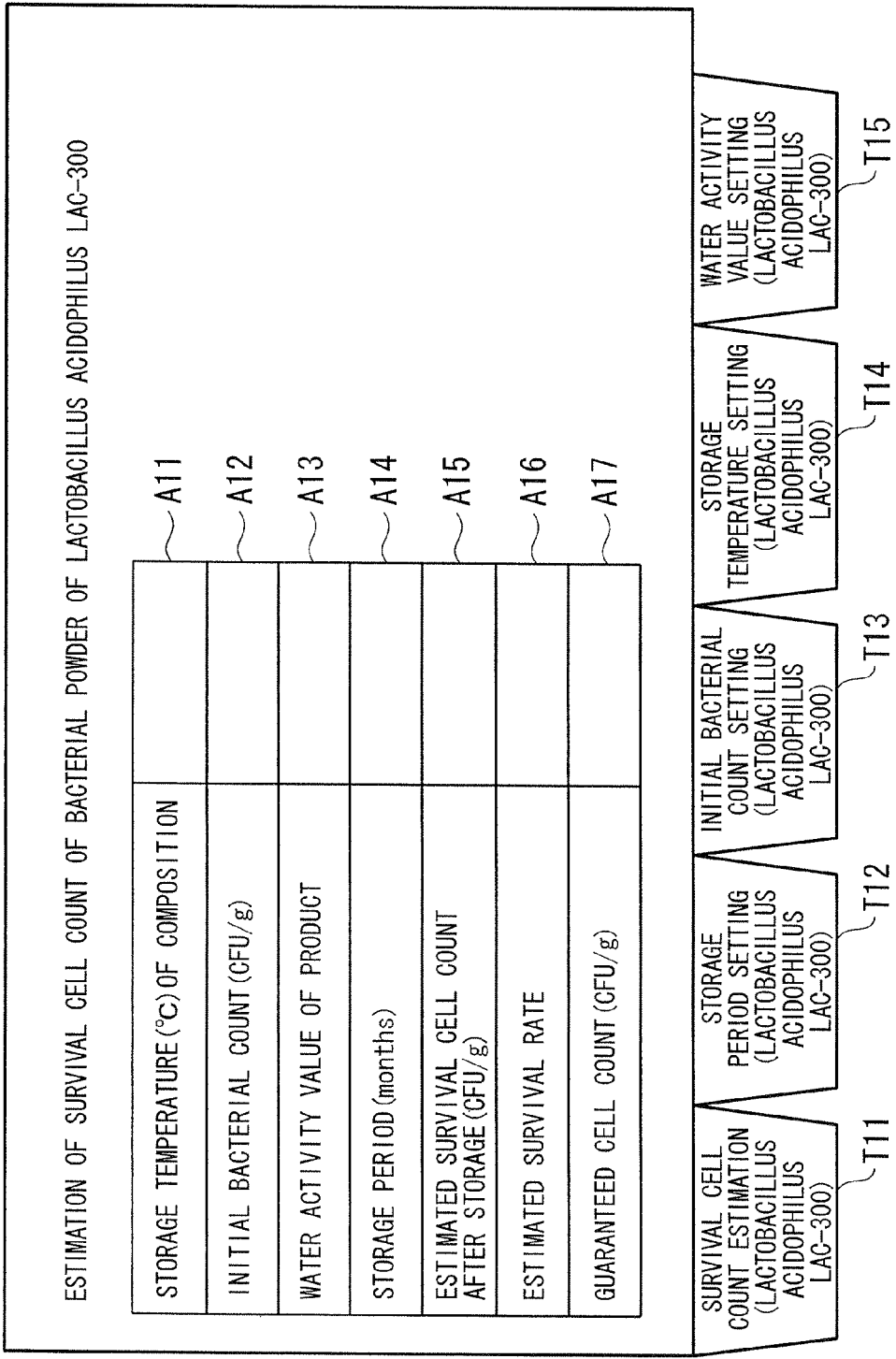
FIG. 14 shows another example of a display screen image output from the device for estimating survival cell count.

FIG. 14 shows another example of an image output from the device 1 for estimating survival cell count.

This image shows the case where *L. acidophilus* LAC-300 is selected as the strain type and the survival cell count of the strain contained in a composition after a storage period (estimated survival cell count) is selected as the calculation object, by selecting the tab T11 with the input unit of the device 1 for estimating survival cell count.

The user enters numerical values into a field an input field A11 for entering a storage temperature (° C.) of the composition, an input field A12 for entering a viable cell count $n_0$ (CFU/g) of the strain contained in the composition at the initiation of storage (initial bacterial count), an input field A13 for entering a water activity value of the composition, and an input field A14 for entering a storage period (months) of the composition containing the strain, by the input unit of the device 1 for estimating survival cell count. Thereby the calculation unit 14 of the device 1 for estimating survival cell count calculates the survival cell count $n_t$ (CFU/g) of the bacterium strain contained in the composition after the storage period, by substituting the values that have been entered into the input fields A11 to A14, into the equation (I) using the $A_T$, $B_T$, $C_T$, and $D_T$ corresponding to the selected strain type, in this case, *L. acidophilus* LAC-300, and the output instruction unit 15 displays the calculation result in the display field A15. The equation (I) using the $A_T$, $B_T$, $C_T$, and $D_T$ corresponding to *L. acidophilus* LAC-300 can be exemplified by the equation (22) in the test example 4.

The output instruction unit 15 further displays the estimated survival rate in the display field A16, and displays the guaranteed cell count N(CFU/g) in the display field A17.

The device 1 for estimating survival cell count may comprises only an input receiver 11, a memory unit 13, a calculation unit 14, and an output instruction unit 15. In this case, the memory unit 13 of the device 1 for estimating survival cell count has $A_T$, $B_T$, $C_T$, and $D_T$ calculated by another device 1 for estimating survival cell count which comprises at least an input receiver 11 and a constant/coefficient calculation unit 12.

The above-mentioned device 1 for estimating survival cell count has a computer system therein. The operation manner of the input receiver 11, the coefficient/constant calculation unit 12, the calculation unit 14, and the output instruction unit 15 of the device 1 for estimating survival cell count is recorded in a computer-readable recording medium in the form of a program. This program is read out and executed by a computer system, by which the above-mentioned process is carried out. The computer system referred to herein includes CPU, various kinds of memories, OS, peripheral equipments, and such hardwares.

In addition, if the WWW system is employed, the term "computer system" also includes homepage providing environments (or display environments).

Moreover, the term "computer-readable recording medium" refers to a portable medium such as a flexible disk, a magneto-optic disk, ROM, and CD-ROM, or a memory device such as a hard disk installed in a computer system. Furthermore, the term "computer-readable recording medium" also includes those dynamically holding a program in a short period of time, such as a communication line for sending a program through a network like an interne or through a communication line like a telephone line, as well as those holding a program for a fixed period of time, such as, in this case, a volatile memory inside a computer system on the server or client side. The object of the above-mentioned program may be to realize a part of the above-mentioned function, or to realize the above-mentioned function when combined with another program already recorded in a computer system.

EXAMPLE

Example 1

A bacterial powder of *B. longum* BAA-999 manufactured by Morinaga Milk Industry Co., Ltd was added to skim milk (manufactured by Morinaga Milk Industry Co., Ltd) having a water activity value of 0.25, at the concentration of $1\times10^8$ (CFU/g) in the powder milk, to thereby produce a milk powder containing bifidobacteria in which the viable cell count $n_0$ (CFU/g) of the strain contained in the composition at the initiation of storage was $1\times10^8$ (CFU/g). This milk powder containing bifidobacteria was sealed up in an aluminum pouch by heat sealing. On the other hand, the survivability of *B. longum* BAA-999 was obtained by the test example 1, and the following relation equation was given.

$$\mathrm{Log}_{10} n_t = \mathrm{Log}_{10} n_0 - t \times \mathrm{EXP}\{(0.1762 \times T + 7.2137)w + (0.18 \times T - 11.178)\} \quad (23)$$

Since this product is supposed to be stored at or under 25° C. and the best-before period was planned to be set at 540 days (18 months), the calculation unit 14 of the device 1 for estimating survival cell count made a calculation of the survival cell count $n_t$ (CFU/g) after the storage period of 540 days at 25° C., in accordance with the equation (23). That is, based on the information received by the input receiver $1\times10^8$ was substituted in $n_0$, $540 \times 1/30 = 18$ was substituted in t, 25 was substituted in T, and 0.25 was substituted in w of the equation (23), by which the following equation was given.

$$\mathrm{Log}_{10} n_{18} = \mathrm{Log}_{10}(1\times10^8) - 18 \times \mathrm{EXP}\{(0.1762 \times 25 + 7.2137) \times 0.25 + (0.18 \times 25 - 11.178)\}$$

Then, $n_{18} = 3.9 \times 10^7$ was obtained from this equation. Accordingly, the survival cell count $n_{18}$ (CFU/g) of the milk powder containing bifidobacteria having the water activity value of 0.25 of the example 1 after 18 months from the initiation of storage when stored at 25° C. was estimated to be $3.9\times10^7$ (CFU/g).

Furthermore, the calculation unit 14 of the device 1 for estimating survival cell count made a calculation of the guaranteed cell count N(CFU/g) of the milk powder containing bifidobacteria of the example 1 within the guarantee period of 540 days when stored at or under 25° C., in accordance with the equation (24). Here, $3.9\times10^7$, which had been obtained from the above-mentioned equation (23), was substituted in $n_t'$ and 0.8 was substituted in a.

$$N = n_t' \times a \quad (24)$$

$N \approx 3.1\times10^7$ was obtained from the equation (24). Thus, the guaranteed cell count N(CFU/g) of the milk powder containing bifidobacteria of the example 1 within the guarantee period of 540 days when stored at or under 25° C. was set at $3.1\times10^7$ (CFU/g).

INDUSTRIAL APPLICABILITY

According to the method for estimating survival cell count of the present invention, it is possible to calculate an accurately estimated result of the survival cell count (CFU/g) of a specific strain in a probiotic product with respect to its storage period, and to apply for a usage to shorten the time for developing the product. Moreover, according to the method for setting guaranteed cell count of the present invention, it is possible to apply for a usage to readily calculate a guaranteed cell count of a specific strain in a probiotic product within its quality guarantee period.

BRIEF DESCRIPTION OF THE REFERENCE SYMBOLS

1 . . . Device for estimating survival cell count
11 . . . Input receiver
12 . . . Constant/coefficient calculation unit
13 . . . Memory unit
14 . . . Calculation unit
15 . . . Output instruction unit

The invention claimed is:

1. A method for estimating survival cell count of a specific strain of a bacterium belonging to bifidobacteria or lactic acid bacteria when a composition containing the specific strain is stored at a constant temperature, the method comprising:
calculating each value of the following $A_T$, $B_T$, $C_T$ and $D_T$ by performing the following steps 1) to 5),
creating the following equation (I) based on said $A_T$, $B_T$, $C_T$, and $D_T$, and
estimating a survival cell count $n_t$ (CFU/g) of the specific strain contained in the composition after storage by the following equation (I), $$\mathrm{Log}_{10} n_t = \mathrm{Log}_{10} n_0 - t \times \mathrm{EXP}\{(A_T \times T + B_T)w + (C_T \times T + D_T)\} \quad (I)$$

t: storage period (days)×1/30
$n_t$: survival cell count (CFU/g) of the strain contained in the composition after the storage period t (days)
$n_0$: viable cell count (CFU/g) of the strain contained in the composition at the initiation of storage
T: storage temperature (° C.)
w: water activity value of the composition
1) the specific strain is respectively added to powdery compositions having at least three different water activity values w and evenly mixed to thereby produce specific strain-containing composition samples,
each sample is then individually packed and sealed up in a plural number, which is defined by number of storage temperature conditions times number of storage period conditions, of moisture barrier containers, by which a plurality of sealed samples are given per each water activity value w,
then, each sealed sample is stored in at least three different storage temperatures (° C.), and
thereafter, the survival cell count $n_t$ (CFU/g) in the composition is measured at at least three time points within the storage period (days);
2) the survival cell counts $n_t$ (CFU/g) within the storage period are plotted by having the common logarithmic value of the survival cell count $n_t$ (CFU/g) of the specific strain in the respective samples which have undergone different storage conditions including storage temperature (° C.) and water activity value on the Y-axis, and the storage period t (days)×1/30 on the X-axis,
the regression line of respective storage condition is calculated using these plots, and a regression coefficient represented by the slope of the regression line of respective storage condition is defined as the inactivation rate;
3) next, by having the natural logarithmic value of the inactivation rate at respective storage temperature (° C.) on the Y-axis and the water activity value w on the X-axis, the relation between both parties is plotted, and using this plot, the regression line represented by the equation: y=ax+b of respective storage temperature (° C.) is respectively calculated;
4) by having the slope (a) of the linear equation of respective storage temperature (° C.) obtained from the step 3) on the Y-axis and the storage temperature T (° C.) on the X-axis, the relation between both parties is plotted, and using this plot, a linear equation is obtained, and the slope $A_T$ and the Y-intercept $B_T$ of the resultant regression line are calculated; and 5) by having the constant (b) of the regression line obtained from the step 3) on the Y-axis and the storage temperature T (° C.) on the X-axis, the relation between both parties is plotted, and
a linear equation thereof is obtained, and the slope $C_T$ and the Y-intercept $D_T$ of the resultant linear equation are calculated.

2. The method for estimating survival cell count according to claim 1, wherein the bacterium belonging to bifidobacteria or lactic acid bacteria is a bacterium selected from the group consisting of *Bifidobacterium longum, Bifidobacterium breve, Bifidobacterium pseudolongum, Lactobacillus gasseri, Lactobacillus acidophilus, Lactobacillus rhamnosus, Lactobacillus plantrum*, and *Enterococcus faecium*.

3. The method for estimating survival cell count according to claim 1, wherein
the specific stain is *Bifidobacterium longum* ATCC BAA-999.

4. The method for estimating survival cell count according to claim 1, wherein
the specific strain is *Bifidobacterium breve* BCCM LMG 23729.

5. The method for estimating survival cell count according to claim 1, wherein
the specific strain is *Bifidobacterium psuedolongum* IFO 15861.

6. The method for estimating survival cell count according to claim 1, wherein
the specific stain is a lactic acid bacterium selected from the group consisting of *Lactobacillus gasseri, Lactobacillus acidophilus, Lactobacillus rhamnosus, Lactobacillus plantrum*, and *Enterococcus faecium*.

7. The method for estimating survival cell count according to claim 1, wherein
the specific strain is *Lactobacillus acidophilus* IFO-15862 (*Lactobacillus acidophilus* LAC-300).

8. The method for estimating survival cell count according to claim 1, wherein the water activity value w of the equation (I) is less than or equal to 0.6.

9. The method for estimating survival cell count according to claim 1, wherein the storage temperature T(° C.) of the equation (I) is 25° C. to 60° C.

10. A method for setting a survival cell count of a specific strain of a bacterium belonging to bifidobacteria or lactic acid bacteria, the method comprising calculating the survival cell count N (CFU/g) within a guarantee period t' (days) between 1 to 1500 days when a composition containing the specific strain is stored at or under the storage temperature T' (° C.) by substituting a value of survival cells $n_t'$ estimated by the method according to claim 1 and a value of constant a in the following equation (II), $$N = n_t' \times a \qquad (II)$$

$n_t'$: survival cell count $n_t$ (CFU/g) of the strain contained in the composition after a storage period t (days), which has been estimated by the method for estimating the survival cell count according to claim 1, assuming that the storage temperature T (° C.) is T' (° C.) and the storage period t (days) is a guarantee period t' (days)
a: constant less than 1.

11. The method for setting a survival cell count according to claim 10, wherein the constant a is from 0.5 to 0.9.

* * * * *